US009708673B2

(12) United States Patent
Charne et al.

(10) Patent No.: US 9,708,673 B2
(45) Date of Patent: *Jul. 18, 2017

(54) *BRASSICA* GAT EVENT AND COMPOSITIONS AND METHODS FOR THE IDENTIFICATION AND/OR DETECTION THEREOF

(71) Applicants: E I DU PONT DE NEMOURS AND COMPANY, Wilmington, DE (US); PIONEER HI BRED INTERNATIONAL INC, Johnston, IA (US)

(72) Inventors: David George Charne, Guelph (CA); Wenpin Chen, Brampton (CA); Chadwick Bruce Koscielny, Miami (CA); Zhongsen Li, Hockessin, DE (US); Jayantilal Devabhai Patel, Thornhill (CA); Ferdinand Thoonen, Guleph (CA); Lomas Tulsieram, Mississauga (CA); Yongping Zhang, Branpton (CA)

(73) Assignees: E I DU PONT DE NEMOURS AND COMPANY, Wilmington, DE (US); PIONEER HI-BRED INTERNATIONAL, INC., Johnston, IA (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/627,881

(22) Filed: Feb. 20, 2015

(65) Prior Publication Data

US 2015/0159229 A1 Jun. 11, 2015

Related U.S. Application Data

(60) Continuation of application No. 14/047,452, filed on Oct. 7, 2013, now Pat. No. 8,993,238, which is a division of application No. 12/953,852, filed on Nov. 24, 2010, now Pat. No. 8,581,046.

(60) Provisional application No. 61/309,385, filed on Mar. 1, 2010, provisional application No. 61/263,923, filed on Nov. 24, 2009.

(51) Int. Cl.

| | |
|---|---|
| ***C12Q 1/68*** | (2006.01) |
| ***A01H 5/10*** | (2006.01) |
| ***C12N 15/82*** | (2006.01) |
| ***A01N 57/20*** | (2006.01) |
| ***C11B 1/00*** | (2006.01) |
| ***A23L 19/00*** | (2016.01) |

(52) U.S. Cl.

CPC ............. *C12Q 1/6895* (2013.01); *A01H 5/10* (2013.01); *A01N 57/20* (2013.01); *A23L 19/00* (2016.08); *C11B 1/00* (2013.01); *C12N 15/8275* (2013.01); *C12Q 2600/13* (2013.01)

(58) Field of Classification Search

None

See application file for complete search history.

(56) References Cited

U.S. PATENT DOCUMENTS

| | | | | |
|---|---|---|---|---|
| 5,188,642 | A | 2/1993 | Shah et al. | |
| 5,625,130 | A | 4/1997 | Grant et al. | |
| 7,405,074 | B2 | 7/2008 | Castle et al. | |
| 7,687,434 | B2 | 3/2010 | DeBillot et al. | |
| 8,581,046 | B2 | 11/2013 | Charne et al. | |
| 8,993,238 | B2 | 3/2015 | Charne et al. | |
| 2003/0226166 | A1 | 12/2003 | Falco et al. | |
| 2004/0082770 | A1 | 4/2004 | Castle et al. | |
| 2004/0123352 | A1 | 6/2004 | Plaisted et al. | |
| 2005/0246798 | A1 | 11/2005 | Castle et al. | |
| 2006/0070139 | A1 | 3/2006 | Bing et al. | |
| 2007/0061917 | A1 | 3/2007 | McCutchen et al. | |
| 2007/0130641 | A1 | 6/2007 | McCutchen et al. | |
| 2008/0051288 | A1 | 2/2008 | Cressman, Jr. et al. | |
| 2008/0108072 | A1 * | 5/2008 | Chicoine ............ | C12N 15/8275 435/6.13 |
| 2009/0011938 | A1 | 1/2009 | Castle et al. | |
| 2009/0137395 | A1 | 5/2009 | Chicoine et al. | |

FOREIGN PATENT DOCUMENTS

| | | |
|---|---|---|
| WO | WO 98/39419 | 9/1998 |
| WO | WO 02/36782 A2 | 5/2002 |
| WO | WO 02/36831 A2 | 5/2002 |
| WO | WO 03/013224 | 2/2003 |

(Continued)

OTHER PUBLICATIONS

U.S. Appl. No. 12/953,835, filed Nov. 24, 2010, Charne et al.
Hegstad, Jeff, "Herbicide Efficacy and Yield Evaluations", CSB Meeting, Feb. 22, 2007.
Hegstad, Jeff, "Herbicide Efficacy and Yield Evaluations", ASA/CSSA/SSSA 2007 International Annual Meetings.

(Continued)

*Primary Examiner* — Aaron Priest

(57) ABSTRACT

Compositions and methods related to transgenic glyphosate tolerant *Brassica* plants are provided. Specifically, the present invention provides *Brassica* plants having a DP-073496-4 event which imparts tolerance to glyphosate. The *Brassica* plant harboring the DP-073496-4 event at the recited chromosomal location comprises genomic/transgene junctions within SEQ ID NO: 2 or with genomic/transgene junctions as set forth in SEQ ID NO: 12 and/or 13. The characterization of the genomic insertion site of the event provides for an enhanced breeding efficiency and enables the use of molecular markers to track the transgene insert in the breeding populations and progeny thereof. Various methods and compositions for the identification, detection, and use of the event are provided.

3 Claims, 6 Drawing Sheets

(56) References Cited

FOREIGN PATENT DOCUMENTS

| | | | | | |
|---|---|---|---|---|---|
| WO | WO 03/052073 | A2 | | 6/2003 | |
| WO | WO 03/092360 | A2 | | 11/2003 | |
| WO | WO 2004/099447 | | | 11/2004 | |
| WO | WO 2005/012515 | A2 | | 2/2005 | |
| WO | WO 2006/039376 | A2 | | 4/2006 | |
| WO | WO 2006121757 | A2 | * | 11/2006 | ........... C07K 14/805 |
| WO | WO 2007/024782 | | | 3/2007 | |
| WO | 2008/112019 | A2 | | 9/2009 | |

OTHER PUBLICATIONS

Castle, L.A., et al., "Discovery and Directed Evolution of a Glyphosate Tolerance Gene", *Science*, vol. 304, No. 21, May 21, 2004, pp. 1151-1154.

Duke, S., et al., "Glyphosate-Resistant Crops and Weeds: Now and in the Future", *AGBIOFORUM*, University of MO, Columbia Agriculutre and Engineering Department, vol. 12, No. 3-4, Jan. 1, 2009, pp. 346-357.

Green, J.M., "Review of Glyphosate and ALS-Inhibiting Herbicide Crop Resistance and Resistant Weed Management", *Weed Technology*, 2007, vol. 21, pp. 547-558.

Green, J.M., et al. "New Multiple-Herbicide Crop Resistance and Formulation Technology to Augment the Utility of Glyphosate", *Pest Management Science*, vol. 64, No. 4, Apr. 4, 2008, pp. 332-339.

Rood, T.A., et al.., "Petition for the Determination of Nonregulated Status for Herbicide Tolerant 356043 Soybean", Sep. 27, 2006.

Terry, C.F. and Harris, N., "Event-Specific Detection of Roundup Ready Soya using two Different Real Time PCR Detection Chemistries", *Eur Food Res Technol.*, vol. 213, 2001, pp. 425-431.

Windels, P., et al., "Characterization of the Roundup Ready Soybean Insert", *Eur Food Res Technol.*, vol. 213, 2001, pp. 107-112.

Windels, P., et al., "Development of a Line Specific GMO Detection Method: A Case Study", *Med. Fac. Landouww. Univ. Gent.*, vol. 64, No. 5B, Sep. 22, 1999, pp. 459-462.

Yang, L., et al., "Event Specific Qualitative and Quantitative Polymerase Chain Reaction Detection of Genetically Modified MON863 Maize Based on the 5'-Transgene Integration Sequence", *Journal of Agricultural and Food Chemistry*, 2005, pp. 9312-9318, vol. 53.

Jerry M. Green et al., Response of 98140 Corn with gat4621 and hra Transgenes to Glyphosate and ALS-Inhibiting Herbicides, Weed Science, 2009, pp. 142-148, vol. 57.

A. Hohe et al., A tool for understanding homologous recombination in plants, Plant Cell Rep, 2003, pp. 1135-1142, vol. 21.

T. Michael Spencer et al, Segregation of transgenes in maize, Plant Molecular Biology, 1992, pp. 201-210, vol. 18.

International Search Report—PCT/US2010/058011—mailed Jun. 17, 2011.

Written Opinion—PCT/US2010/058011—mailed Jun. 17, 2011.

* cited by examiner

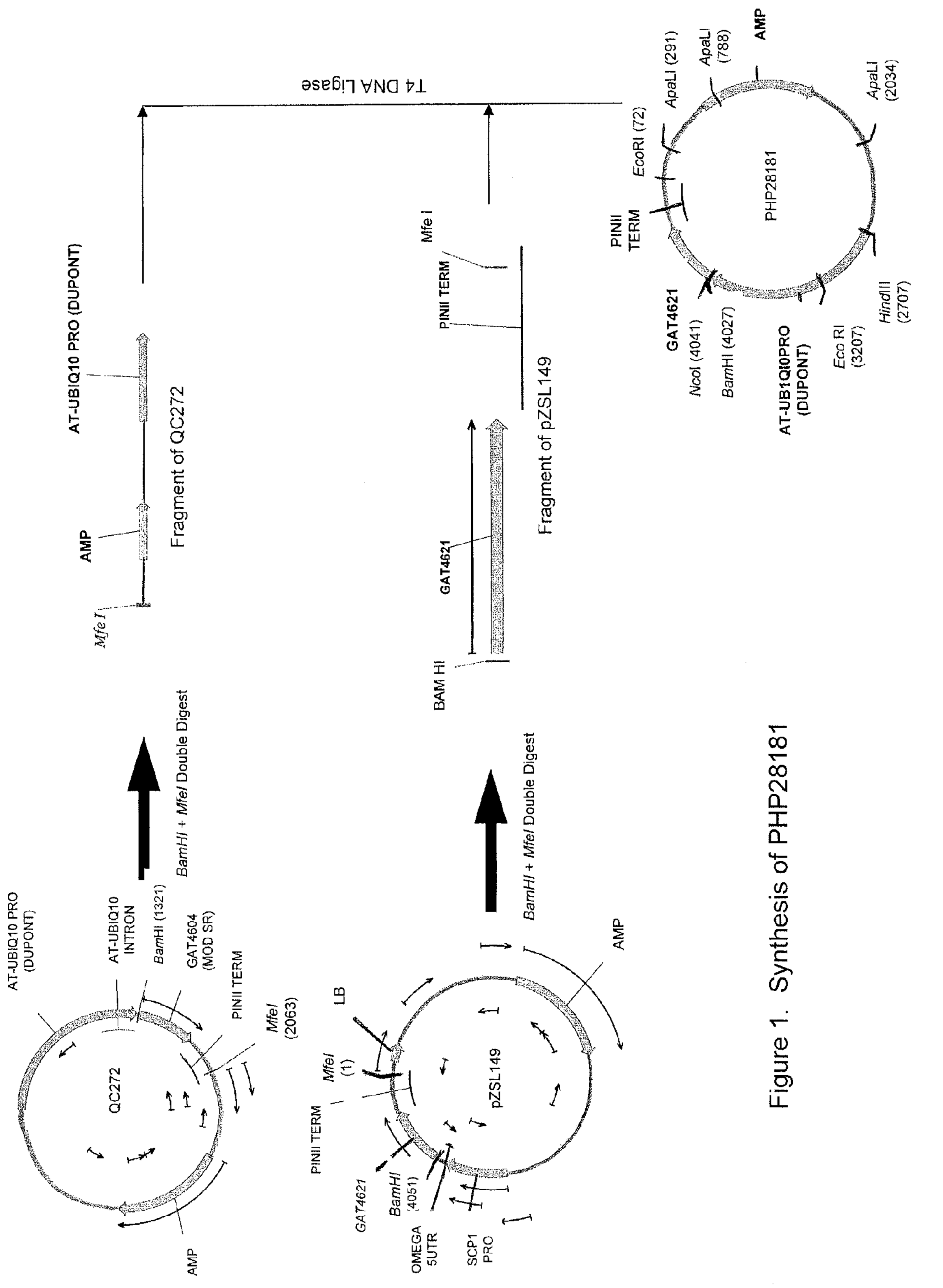
Figure 1. Synthesis of PHP28181

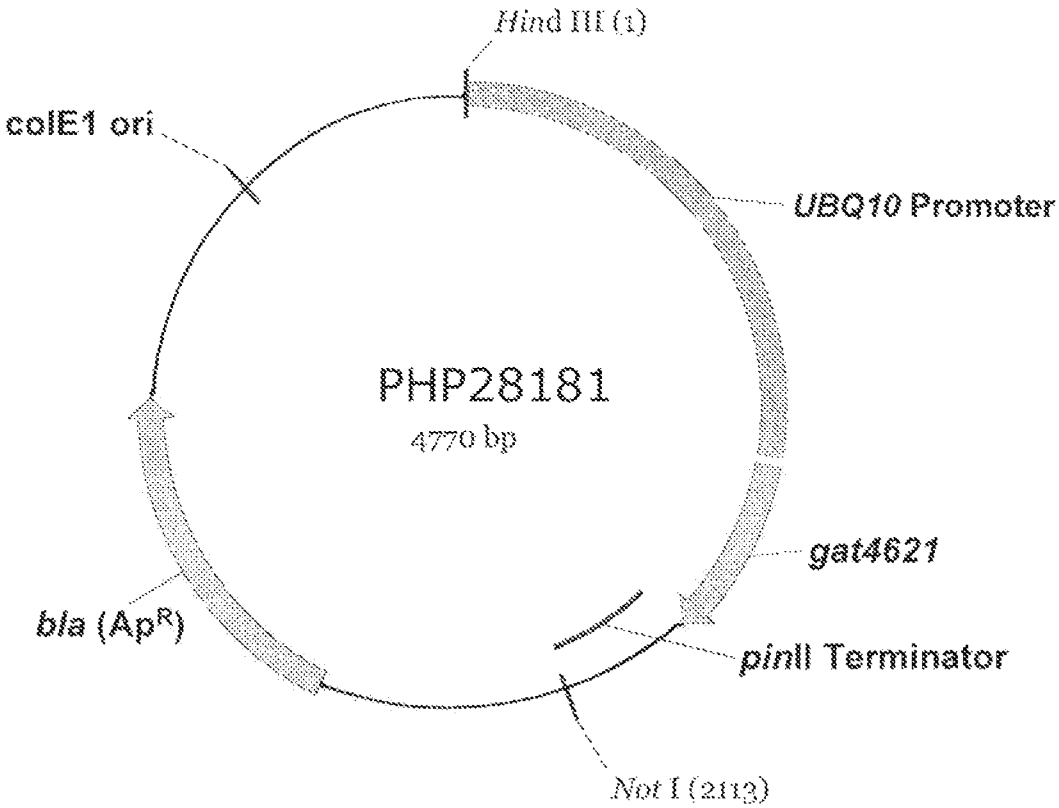
Figure 2. Schematic diagram of plasmid PHP28181

Figure 3. Schematic diagram of Fragment PHP28181A.
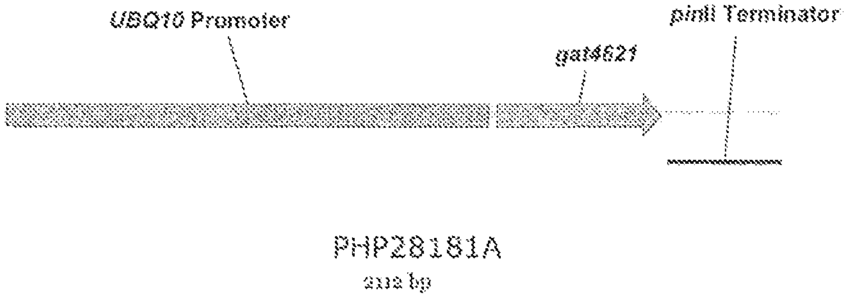

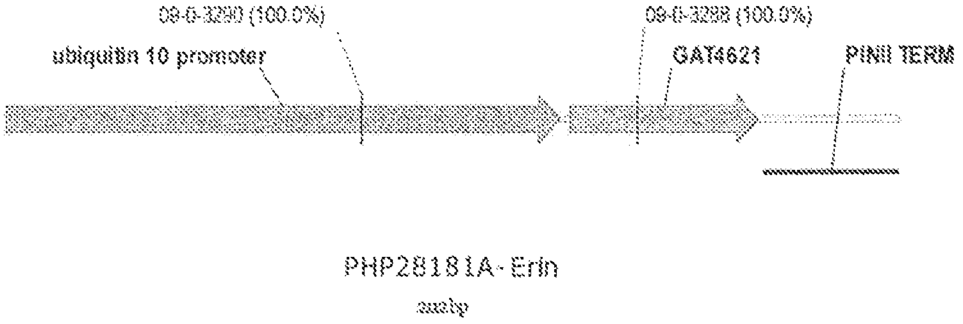
FIGURE 4: SCHEMATIC REPRESENTATION OF FRAGMENT A FROM PHP28181 (PHP28181A)

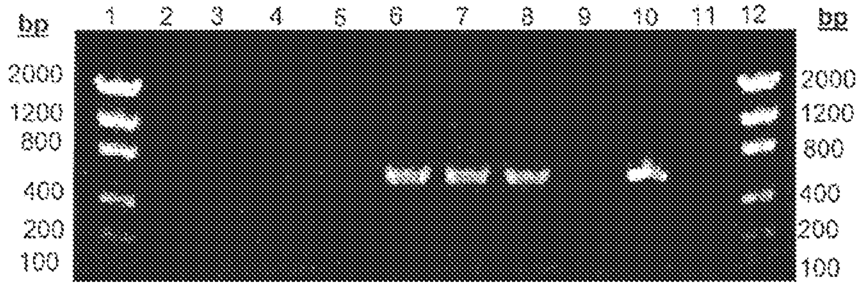
Figure 5: PCR Analysis of Leaf DNA From DP-073496-4 Brassica and Non-Genetically Modified Control Brassica

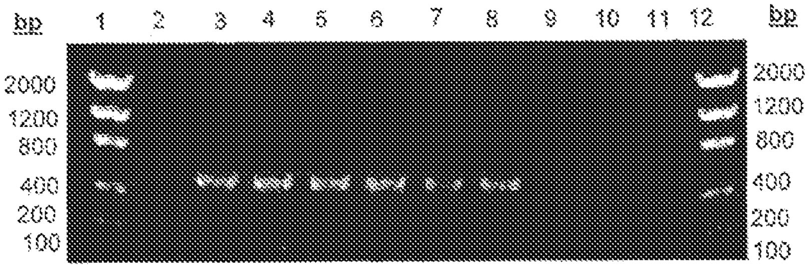
Figure 6: FatA Gene PCR Analysis of Leaf DNA From DP-073496-4 Brassica and Non-Genetically Modified Control Brassica

SEQUENCE LISTING

```
<160> NUMBER OF SEQ ID NOS: 27

<210> SEQ ID NO 1
<211> LENGTH: 147
<212> TYPE: PRT
<213> ORGANISM: Artificial Sequence
<220> FEATURE:
<223> OTHER INFORMATION: GAT4621 protein encoded by shuffled gat4621
      gene

<400> SEQUENCE: 1

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Ala Cys Met Phe
            20                  25                  30

Glu Ser Asp Leu Thr Arg Ser Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
            100                 105                 110

Thr Ser Ala Ser Gly Tyr Tyr Arg Lys Leu Gly Phe Ser Glu Gln Gly
        115                 120                 125

Glu Val Phe Asp Thr Pro Pro Val Gly Pro His Ile Leu Met Tyr Lys
    130                 135                 140

Arg Ile Thr
145


<210> SEQ ID NO 2
```

<211> LENGTH: 3104
<212> TYPE: DNA
<213> ORGANISM: Artificial Sequence
<220> FEATURE:
<223> OTHER INFORMATION: DP073496-4 insert and flanking genomic sequence

<400> SEQUENCE: 2

```
aaaaaaaaaa aaatcatctg taaataattg taaaggttaa ttcattatat ttaaaagatt     60

cggtttaatg tttatatatg atcgagaata atatagtttt ggtccaattt agagtcgaat    120

cttaataatg ttgtggtatc aagagaatcc attgtgctgg tccaattcag atatggtttt    180

ctgttttttt atttaatatt attttttaaa atgttgtata atttcgtttc agacgcaaac    240

aaattacact ttttcctttc aattgaatat agcattacat aaaaatcaag agaatccatt    300

tgttcctaaa cataaattaa tttttgttct gttttcagtt ttgtttcggc tgttcacttg    360

ttcgttggag ttgtctactg cttgctgagc tggtccgtgg gccttcctaa acgtgccgta    420

agttcttctc ttcatagctc attacagttt tcattagtta gatcaggata ttcttgttta    480

agatgttgaa ctctatggag gtttgtatga actgatgatc taggaccgga taagttccct    540

tcttcatagc gaacttattc aaagaatgtt ttgtgtatca ttcttgttac attgttatta    600

atgaaaaaat attattggtc attggactga acacgagtgt taaatatgga ccaggcccca    660

aataagatcc attgatatat gaattaaata acaagaataa atcgagtcac caaaccactt    720

gccttttttta acgagacttg ttcaccaact tgatacaaaa gtcattatcc tatgcaaatc    780

aataatcata caaaaatatc caataacact aaaaaattaa aagaaatgga taatttcaca    840

atatgttata cgataaagaa gttacttttc caagaaattc actgatttta taagcccact    900

tgcattagat aaatggcaaa aaaaaacaaa aaggaaaaga aataaagcac gaagaattct    960

agaaaatacg aaatacgctt caatgcagtg ggacccacgg ttcaattatt gccaattttc   1020

agctccaccg tatatttaaa aaataaaacg ataatgctaa aaaaatataa atcgtaacga   1080

tcgttaaatc tcaacggctg gatcttatga cgaccgttag aaattgtggt tgtcgacgag   1140

tcagtaataa acggcgtcaa agtggttgca gccggcacac acgagtcgtg tttatcaact   1200

caaagcacaa atacttttcc tcaacctaaa aataaggcaa ttagccaaaa acaactttgc   1260

gtgtaaacaa cgctcaatac acgtgtcatt ttattattag ctattgcttc accgccttag   1320

ctttctcgtg acctagtcgt cctcgtcttt tcttcttctt cttctataaa acaataccca   1380

aagagctctt cttcttcaca attcagattt caatttctca aaatcttaaa aactttctct   1440

caattctctc taccgtgatc aaggtaaatt tctgtgttcc ttattctctc aaaatcttcg   1500

attttgtttt cgttcgatcc caatttcgta tatgttcttt ggtttagatt ctgttaatct   1560

tagatcgaag acgattttct gggtttgatc gttagatatc atcttaattc tcgattaggg   1620

tttcatagat atcatccgat ttgttcaaat aatttgagtt ttgtcgaata attactcttc   1680

gatttgtgat ttctatctag atctggtgtt agtttctagt ttgtgcgatc gaatttgtcg   1740

attaatctga gtttttctga ttaacagcgg ccgggatcca cacgacacca tggctattga   1800

ggttaagcct atcaacgcag aggataccta tgaccttagg catagagtgc tcagaccaaa   1860

ccagcctatc gaagcctgca tgtttgagtc tgaccttact aggagtgcat ttcaccttgg   1920

tggattctac ggaggtaaac tgatttccgt ggcttcattc caccaagctg agcactctga   1980

acttcaaggt aagaagcagt accagcttag aggtgtggct accttggaag gttatagaga   2040

gcagaaggct ggttccagtc tcgtgaaaca cgctgaagag attctcagaa agagaggtgc   2100

tgacatgatc tggtgtaatg ccaggacatc tgcttcagga tactacagga agttgggatt   2160
```

```
cagtgagcaa ggagaggtgt tcgatactcc tccagttgga cctcacatcc tgatgtataa   2220

gaggatcaca taactagcta gtcagttaac ctagacttgt ccatcttctg gattggccaa   2280

cttaattaat gtatgaaata aaaggatgca cacatagtga catgctaatc actataatgt   2340

gggcatcaaa gttgtgtgtt atgtgtaatt actagttatc tgaataaaag agaaagagat   2400

catccatatt tcttatccta aatgaatgtc acgtgtcttt ataattcttt gatgaaccag   2460

atgcatttca ttaaccaaat ccatatacat ataaatatta atcatatata attaatatca   2520

attgggttag caaaacaaat ctagtctagg tgtgttttgc gaatgcgaca gtccgtaact   2580

tggactaaac aaattgacct aaaaacatga gcataactaa aactcccatg taatggttaa   2640

actataacca acaaatctca aactatgaga tataacacaa gacatctttg agaaattcta   2700

aaccgtagaa taatctctta caaaaaatac tccaaactat ggaaaaacaa cactgagata   2760

ttctaaacta tagaataaat ctcaggaaaa gaattagccc atgtgaaagg cacaaaccgt   2820

taacattact aaaaccctcg aattctttkg cactgatcac ccgacgaaaa cccaagaaaa   2880

taaattagat aaataaaaaa aaccaaaacc ctaataaaaa aacaaaacct aacttcrcgt   2940

gaatcaacgt cgtcatccgg atcatcttca ccgtcttcat cgtcaacacc accgatgaac   3000

gccatcaaag ctctaaaatt ataatgcgga agttttaatt tcgatcccaa agaatcgtct   3060

gctctgatac catgtaaagt ataatagaat ataatatatt attg                    3104


<210> SEQ ID NO 3
<211> LENGTH: 2112
<212> TYPE: DNA
<213> ORGANISM: Artificial Sequence
<220> FEATURE:
<223> OTHER INFORMATION: PHP28181A

<400> SEQUENCE: 3

agcttagatc aggatattct tgtttaagat gttgaactct atggaggttt gtatgaactg     60

atgatctagg accggataag ttcccttctt catagcgaac ttattcaaag aatgttttgt    120

gtatcattct tgttacattg ttattaatga aaaaatatta ttggtcattg gactgaacac    180

gagtgttaaa tatggaccag gccccaaata agatccattg atatatgaat taaataacaa    240

gaataaatcg agtcaccaaa ccacttgcct tttttaacga gacttgttca ccaacttgat    300

acaaaagtca ttatcctatg caaatcaata atcatacaaa aatatccaat aacactaaaa    360

aattaaaaga aatggataat ttcacaatat gttatacgat aaagaagtta cttttccaag    420

aaattcactg attttataag cccacttgca ttagataaat ggcaaaaaaa aacaaaaagg    480

aaaagaaata aagcacgaag aattctagaa aatacgaaat acgcttcaat gcagtgggac    540

ccacggttca attattgcca attttcagct ccaccgtata tttaaaaaat aaaacgataa    600

tgctaaaaaa atataaatcg taacgatcgt taaatctcaa cggctggatc ttatgacgac    660

cgttagaaat tgtggttgtc gacgagtcag taataaacgg cgtcaaagtg gttgcagccg    720

gcacacacga gtcgtgttta tcaactcaaa gcacaaatac ttttcctcaa cctaaaaata    780

aggcaattag ccaaaaacaa ctttgcgtgt aaacaacgct caatacacgt gtcattttat    840

tattagctat tgcttcaccg ccttagcttt ctcgtgacct agtcgtcctc gtcttttctt    900

cttcttcttc tataaaacaa tacccaaaga gctcttcttc ttcacaattc agatttcaat    960

ttctcaaaat cttaaaaact ttctctcaat tctctctacc gtgatcaagg taaatttctg   1020

tgttccttat tctctcaaaa tcttcgattt tgttttcgtt cgatcccaat ttcgtatatg   1080
```

-continued

```
ttctttggtt tagattctgt taatcttaga tcgaagacga ttttctgggt ttgatcgtta   1140

gatatcatct taattctcga ttagggtttc atagatatca tccgatttgt tcaaataatt   1200

tgagttttgt cgaataatta ctcttcgatt tgtgatttct atctagatct ggtgttagtt   1260

tctagtttgt gcgatcgaat ttgtcgatta atctgagttt ttctgattaa cagcggccgg   1320

gatccacacg acaccatggc tattgaggtt aagcctatca acgcagagga tacctatgac   1380

cttaggcata gagtgctcag accaaaccag cctatcgaag cctgcatgtt tgagtctgac   1440

cttactagga gtgcatttca ccttggtgga ttctacggag gtaaactgat ttccgtggct   1500

tcattccacc aagctgagca ctctgaactt caaggtaaga agcagtacca gcttagaggt   1560

gtggctacct tggaaggtta tagagagcag aaggctggtt ccagtctcgt gaaacacgct   1620

gaagagattc tcagaaagag aggtgctgac atgatctggt gtaatgccag gacatctgct   1680

tcaggatact acaggaagtt gggattcagt gagcaaggag aggtgttcga tactcctcca   1740

gttggacctc acatcctgat gtataagagg atcacataac tagctagtca gttaacctag   1800

acttgtccat cttctggatt ggccaactta attaatgtat gaaataaaag gatgcacaca   1860

tagtgacatg ctaatcacta taatgtgggc atcaaagttg tgtgttatgt gtaattacta   1920

gttatctgaa taaaagagaa agagatcatc catatttctt atcctaaatg aatgtcacgt   1980

gtctttataa ttctttgatg aaccagatgc atttcattaa ccaaatccat atacatataa   2040

atattaatca tatataatta atatcaattg ggttagcaaa acaaatctag tctaggtgtg   2100

ttttgcgaat gc                                                       2112


<210> SEQ ID NO 4
<211> LENGTH: 23
<212> TYPE: DNA
<213> ORGANISM: Artificial Sequence
<220> FEATURE:
<223> OTHER INFORMATION: primer for ubiquitin promoter

<400> SEQUENCE: 4

agctattgct tcaccgcctt agc                                             23


<210> SEQ ID NO 5
<211> LENGTH: 25
<212> TYPE: DNA
<213> ORGANISM: Artificial Sequence
<220> FEATURE:
<223> OTHER INFORMATION: primer for gat4621

<400> SEQUENCE: 5

gctcagcttg gtggaatgaa gccac                                           25


<210> SEQ ID NO 6
<211> LENGTH: 31
<212> TYPE: DNA
<213> ORGANISM: Artificial Sequence
<220> FEATURE:
<223> OTHER INFORMATION: primer for canola endogenous FatA

<400> SEQUENCE: 6

gacacaaggc ggcttcaaag agttacagat g                                    31


<210> SEQ ID NO 7
<211> LENGTH: 30
<212> TYPE: DNA
<213> ORGANISM: Artificial Sequence
<220> FEATURE:
<223> OTHER INFORMATION: primer for canola endogenous FatA
```

<400> SEQUENCE: 7
acaatgtcat cttgctggca ttctcttctg 30

<210> SEQ ID NO 8
<211> LENGTH: 2065
<212> TYPE: DNA
<213> ORGANISM: Artificial Sequence
<220> FEATURE:
<223> OTHER INFORMATION: right border genomic sequence

<400> SEQUENCE: 8
gacagtccgt aacttggact aaacaaattg acctaaaaac atgagcataa ctaaaactcc 60
catgtaatgg ttaaactata accaacaaat ctcaaactat gagatataac acaagacatc 120
tttgagaaat tctaaaccgt agaataatct cttacaaaaa atactccaaa ctatggaaaa 180
acaacactga gatattctaa actatagaat aaatctcagg aaaagaatta gcccatgtga 240
aaggcacaaa ccgttaacat tactaaaacc ctcgaattct tttgcactga tcacccgacg 300
aaaacccaag aaaataaatt agataaataa aaaaaaccaa aaccctaata aaaaaacaaa 360
acctaacttc acgtgaatca acgtcgtcat ccggatcatc ttcaccgtct tcatcgtcaa 420
caccaccgat gaacgccatc aaagctctaa aattataatg cggaagtttt aatttcgatc 480
ccaaagaatc gtctgctctg ataccatgta aagtataata gaatataata tattattgtg 540
ttgtatttga taagagaata caatatgcat atatatagtg gtaacattaa cataatgtta 600
acactagata atgctaactt tcctaaacac ttaatgtaaa tatgctaaga atatcttgtg 660
attaacttgc tcttcaagtc tttcctttta gtcttgaggg tcttcatggg tttcacgggc 720
ttcacaatct aggtctgtaa gatacatatc ttccagtcca acatatttct aatatgctga 780
ttcctgaaac acccggatga gtaattttta gatgatacat tgaaaattct aagtaaggat 840
cgaacattga gcaattttaa aaattaagtc aaaactctta cagtagtttt atagtcatat 900
actgtttacg aacagttttg gtgtttttta attagttttg ccgaagtttg tttctgcttt 960
gagtgctgac tcaacaccgt tttggtgttc tttgctatta ttaactctaa gatttaagat 1020
tgtttatgtt tttttgttga tacctctttt atcttaaaat attttttggt gtgtattcca 1080
ttgaaagttt aaagtaattt gtataaaaat aacaaattct ttcaaacatg aattttaaaa 1140
ttttatttaa aattatatta tcgaatttta aagtactatt aaatttaatg ttactaaaaa 1200
tattttaagt tgtgagtttt ataagttttt tagtgctacg tggagttttt tagttaaaat 1260
taaaaatctt ttatgatttt aggtgagact ctaagtggta taacaaaatt catattaaat 1320
tctttagttc atctaaaact cattaagttt tatcccttat ataaaagaat gagatatatg 1380
taatatataa aatgattagt ctttttgcaa aaaaagagta aatagtattt caagaaacga 1440
aaattaatgt tttatggagt gcgatgaaca aaatgtaaca tttataaact tggttccatg 1500
tcaaaaaaaa tgtaaaaacg tataaaaatt caattgatac tttagccatt cagcttagtg 1560
actactagct agcatgccaa aaagtggcaa tacaaacttg aagtattgat taagagatcg 1620
agcggggact ggaacagaag gaaagactgg agacaaattg aacaaacgac aaataaaacg 1680
agcaagaaat taattcatca tgtcgcctga acaaatggca attcctctca agaagcagag 1740
aaagcccact aaatctgtgt tgggacactt gtctgaaacc aaaatctggt cttcgacata 1800
aaaacaatgc attactaaac ttgtcctcta agccggctag atgaaaggaa caacatcacc 1860
actctgaaac cttactacat cctcccgaag gaaagtgaac cgtgaagcac aacaaacgaa 1920
taaattcctc tacatgtaat tgctaaacgt gcaaatcaaa ttcaggacaa taagcaacac 1980
caaatataaa aatcagggga gatgagatag caagaattga ggtcgaagag agttgaattt 2040
acagggagca gagctcacac ctcca 2065

<210> SEQ ID NO 9
<211> LENGTH: 2003
<212> TYPE: DNA
<213> ORGANISM: Artificial Sequence
<220> FEATURE:
<223> OTHER INFORMATION: left border genomic sequence

<400> SEQUENCE: 9
ctttcctgtg actctgtcac gttcatagat ttgaagacca ctcaacacaa tgataataag 60
aggaaaaata tctacagaag tttatatcaa caattacaat tattatagag aaaaagataa 120
aaatagcact aaatcaagtt tttgttccca aactagcatt caaagtcaaa aatcacaaaa 180
ataacactaa atgttttatc aaaaatcaca aacttagggt ttagagttaa agggtggggt 240
ttaggattta gggtttaggg tttagggttt agagtttagg gtttagggtt tagattttag 300
ggtttagggt ttagggttta gggtttagag tttagggttt agggtttatg gtttagggtt 360
tagggtttag agttgagaaa tgaggttttg gggataagat ttcaaatttt gaaaaataaa 420
aaaattaaaa ttttcaaagg ataaacttag aaaggtgcta ttttggtcat tttagttttt 480
gagtgctatt tttgtgatat aaacttagaa atgtgctatt ttggagattt gtcatttatt 540
atattcaaaa gaacaaaaca ttatacaaaa cagataaata gacgacgatg atgatgtgga 600
aattcagacg gccaatactc actctgtctt tccagccata cactttaaga taagatgggc 660
cctacagtca tccaacctaa gccaataatc tcacgattct tatctaatct catctttcct 720
caccgttaga tcatattaca ctatcgatcc ccatgtcata tggtacaccg cgatacactt 780
gataacgaag tatccactct tgaaatacgc gaaaaccaca tactccgctt ccttccctct 840
cactgtcaca actcatcgtt ccaaaaaacc cactgtatca acctcgacga tggagtcacg 900
cgtgctgcta cgcgccacag tcaccggagt accgcaattg agacgaccga tcggtgcgat 960
ccaccgtcag gtcagcactg cgtcgtcgtt ctcggctttt aggttttcag ctccgatcgg 1020
atcagtcgga gagggaggga acctgatctc cggtcgtcag ctccgtccga ttctcctcct 1080
cgatagctcg ccggagaaga gagagattct caagccggtt agagccgccg ctggagattc 1140
agctgggtaa gcaatgaggt ccgtttctgg ctcacttggt gttgactcgt ttgactcgag 1200
tgatctgact cgtttatttg cagggaggcg aaggttggat tcctcgggaa gtatccgtgg 1260
ctcgtcaccg gattcttctt cttcatgtgg tacgtgtgtc cctcacgcgc ttttgcggct 1320
ttaccgccaa agtttgatag cgtggattta cggttttgac cccttgttga tttttattac 1380
aggtacttct tgaatgtgat tttcaacatc cttaataaga agatctataa ttacttcccc 1440
tatccctagt aagtaaaata catttaaatt gtttttgaca tatgaaaaaa tttacattta 1500
catacattga tatctagtct ttttgtatct ctatttgatc atctgtaaaa aaaaaaaaat 1560
catctgtaaa taattgtaaa ggttaattca ttatatttaa aagattcggt ttaatgttta 1620
tatatgatcg agaataatat agttttggtc caatttagag tcgaatctta ataatgttgt 1680
ggtatcaaga gaatccattg tgctggtcca attcagatat ggttttctgt ttttttattt 1740
aatattattt tttaaaatgt tgtataattt cgtttcagac gcaaacaaat tacacttttt 1800
cctttcaatt gaatatagca ttacataaaa atcaagagaa tccatttgtt cctaaacata 1860
aattaatttt tgttctgttt tcagttttgt ttcggctgtt cacttgttcg ttggagttgt 1920
ctactgcttg ctgagctggt ccgtgggcct tcctaaacgt gccgtaagtt cttctcttca 1980
tagctcatta cagttttcat tag 2003

<210> SEQ ID NO 10
<211> LENGTH: 2109
<212> TYPE: DNA
<213> ORGANISM: Artificial Sequence
<220> FEATURE:
<223> OTHER INFORMATION: complete internal transgene

<400> SEQUENCE: 10
ttagatcagg atattcttgt ttaagatgtt gaactctatg gaggtttgta tgaactgatg 60
atctaggacc ggataagttc ccttcttcat agcgaactta ttcaaagaat gttttgtgta 120
tcattcttgt tacattgtta ttaatgaaaa aatattattg gtcattggac tgaacacgag 180
tgttaaatat ggaccaggcc ccaaataaga tccattgata tatgaattaa ataacaagaa 240
taaatcgagt caccaaacca cttgcctttt ttaacgagac ttgttcacca acttgataca 300
aaagtcatta tcctatgcaa atcaataatc atacaaaaat atccaataac actaaaaaat 360
taaaagaaat ggataatttc acaatatgtt atacgataaa gaagttactt ttccaagaaa 420
ttcactgatt ttataagccc acttgcatta gataaatggc aaaaaaaaac aaaaaggaaa 480
agaaataaag cacgaagaat tctagaaaat acgaaatacg cttcaatgca gtgggaccca 540
cggttcaatt attgccaatt ttcagctcca ccgtatattt aaaaaataaa acgataatgc 600
taaaaaaata taaatcgtaa cgatcgttaa atctcaacgg ctggatctta tgacgaccgt 660
tagaaattgt ggttgtcgac gagtcagtaa taaacggcgt caaagtggtt gcagccggca 720
cacacgagtc gtgtttatca actcaaagca caaatacttt tcctcaacct aaaaataagg 780
caattagcca aaaacaactt tgcgtgtaaa caacgctcaa tacacgtgtc attttattat 840
tagctattgc ttcaccgcct tagctttctc gtgacctagt cgtcctcgtc ttttcttctt 900
cttcttctat aaaacaatac ccaaagagct cttcttcttc acaattcaga tttcaatttc 960
tcaaaatctt aaaaactttc tctcaattct ctctaccgtg atcaaggtaa atttctgtgt 1020
tccttattct ctcaaaatct tcgattttgt tttcgttcga tcccaatttc gtatatgttc 1080
tttggtttag attctgttaa tcttagatcg aagacgattt tctgggtttg atcgttagat 1140
atcatcttaa ttctcgatta gggtttcata gatatcatcc gatttgttca aataatttga 1200
gttttgtcga ataattactc ttcgatttgt gatttctatc tagatctggt gttagtttct 1260
agtttgtgcg atcgaatttg tcgattaatc tgagtttttc tgattaacag cggccgggat 1320
ccacacgaca ccatggctat tgaggttaag cctatcaacg cagaggatac ctatgacctt 1380
aggcatagag tgctcagacc aaaccagcct atcgaagcct gcatgtttga gtctgacctt 1440
actaggagtg catttcacct tggtggattc tacggaggta aactgatttc cgtggcttca 1500
ttccaccaag ctgagcactc tgaacttcaa ggtaagaagc agtaccagct tagaggtgtg 1560
gctaccttgg aaggttatag agagcagaag gctggttcca gtctcgtgaa acacgctgaa 1620
gagattctca gaaagagagg tgctgacatg atctggtgta atgccaggac atctgcttca 1680
ggatactaca ggaagttggg attcagtgag caaggagagg tgttcgatac tcctccagtt 1740
ggacctcaca tcctgatgta taagaggatc acataactag ctagtcagtt aacctagact 1800
tgtccatctt ctggattggc caacttaatt aatgtatgaa ataaaaggat gcacacatag 1860
tgacatgcta atcactataa tgtgggcatc aaagttgtgt gttatgtgta attactagtt 1920

```
atctgaataa aagagaaaga gatcatccat atttcttatc ctaaatgaat gtcacgtgtc   1980

tttataattc tttgatgaac cagatgcatt tcattaacca aatccatata catataaata   2040

ttaatcatat ataattaata tcaattgggt tagcaaaaca aatctagtct aggtgtgttt   2100

tgcgaatgc                                                           2109


<210> SEQ ID NO 11
<211> LENGTH: 6177
<212> TYPE: DNA
<213> ORGANISM: Artificial Sequence
<220> FEATURE:
<223> OTHER INFORMATION: complete flanking and internal transgene

<400> SEQUENCE: 11

ctttcctgtg actctgtcac gttcatagat ttgaagacca ctcaacacaa tgataataag     60

aggaaaaata tctacagaag tttatatcaa caattacaat tattatagag aaaaagataa    120

aaatagcact aaatcaagtt tttgttccca aactagcatt caaagtcaaa aatcacaaaa    180

ataacactaa atgttttatc aaaaaatcaca aacttagggt ttagagttaa agggtggggt   240

ttaggattta gggtttaggg tttagggttt agagtttagg gtttagggtt tagattttag    300

ggtttagggt ttagggttta gggtttagag tttagggttt agggtttatg gtttagggtt    360

tagggtttag agttgagaaa tgaggttttg gggataagat ttcaaatttt gaaaaataaa    420

aaaattaaaa ttttcaaagg ataaacttag aaaggtgcta ttttggtcat tttagttttt    480

gagtgctatt tttgtgatat aaacttagaa atgtgctatt ttggagattt gtcatttatt    540

atattcaaaa gaacaaaaca ttatacaaaa cagataaata gacgacgatg atgatgtgga    600

aattcagacg gccaatactc actctgtctt tccagccata cactttaaga taagatgggc    660

cctacagtca tccaacctaa gccaataatc tcacgattct tatctaatct catctttcct    720

caccgttaga tcatattaca ctatcgatcc ccatgtcata tggtacaccg cgatacactt    780

gataacgaag tatccactct tgaaatacgc gaaaaccaca tactccgctt ccttccctct    840

cactgtcaca actcatcgtt ccaaaaaacc cactgtatca acctcgacga tggagtcacg    900

cgtgctgcta cgcgccacag tcaccggagt accgcaattg agacgaccga tcggtgcgat    960

ccaccgtcag gtcagcactg cgtcgtcgtt ctcggctttt aggttttcag ctccgatcgg   1020

atcagtcgga gagggaggga acctgatctc cggtcgtcag ctccgtccga ttctcctcct   1080

cgatagctcg ccggagaaga gagagattct caagccggtt agagccgccg ctggagattc   1140

agctgggtaa gcaatgaggt ccgtttctgg ctcacttggt gttgactcgt ttgactcgag   1200

tgatctgact cgtttatttg cagggaggcg aaggttggat tcctcgggaa gtatccgtgg   1260

ctcgtcaccg gattcttctt cttcatgtgg tacgtgtgtc cctcacgcgc ttttgcggct   1320

ttaccgccaa agtttgatag cgtggattta cggttttgac cccttgttga tttttattac   1380

aggtacttct tgaatgtgat tttcaacatc cttaataaga agatctataa ttacttcccc   1440

tatccctagt aagtaaaata catttaaatt gtttttgaca tatgaaaaaa tttacattta   1500

catacattga tatctagtct ttttgtatct ctatttgatc atctgtaaaa aaaaaaaaat   1560

catctgtaaa taattgtaaa ggttaattca ttatatttaa aagattcggt ttaatgttta   1620

tatatgatcg agaataatat agttttggtc caatttagag tcgaatctta ataatgttgt   1680

ggtatcaaga gaatccattg tgctggtcca attcagatat ggttttctgt ttttttattt   1740

aatattattt tttaaaatgt tgtataattt cgtttcagac gcaaacaaat tacacttttt   1800

cctttcaatt gaatatagca ttacataaaa atcaagagaa tccatttgtt cctaaacata   1860
```

```
aattaatttt tgttctgttt tcagttttgt ttcggctgtt cacttgttcg ttggagttgt   1920
ctactgcttg ctgagctggt ccgtgggcct tcctaaacgt gccgtaagtt cttctcttca   1980
tagctcatta cagttttcat tagttagatc aggatattct tgtttaagat gttgaactct   2040
atggaggttt gtatgaactg atgatctagg accggataag ttcccttctt catagcgaac   2100
ttattcaaag aatgttttgt gtatcattct tgttacattg ttattaatga aaaaatatta   2160
ttggtcattg gactgaacac gagtgttaaa tatggaccag gccccaaata agatccattg   2220
atatatgaat taaataacaa gaataaatcg agtcaccaaa ccacttgcct tttttaacga   2280
gacttgttca ccaacttgat acaaaagtca ttatcctatg caaatcaata atcatacaaa   2340
aatatccaat aacactaaaa aattaaaaga aatggataat ttcacaatat gttatacgat   2400
aaagaagtta cttttccaag aaattcactg attttataag cccacttgca ttagataaat   2460
ggcaaaaaaa aacaaaaagg aaaagaaata aagcacgaag aattctagaa aatacgaaat   2520
acgcttcaat gcagtgggac ccacggttca attattgcca attttcagct ccaccgtata   2580
tttaaaaaat aaaacgataa tgctaaaaaa atataaatcg taacgatcgt taaatctcaa   2640
cggctggatc ttatgacgac cgttagaaat tgtggttgtc gacgagtcag taataaacgg   2700
cgtcaaagtg gttgcagccg gcacacacga gtcgtgttta tcaactcaaa gcacaaatac   2760
ttttcctcaa cctaaaaata aggcaattag ccaaaaacaa ctttgcgtgt aaacaacgct   2820
caatacacgt gtcattttat tattagctat tgcttcaccg ccttagcttt ctcgtgacct   2880
agtcgtcctc gtcttttctt cttcttcttc tataaaacaa tacccaaaga gctcttcttc   2940
ttcacaattc agatttcaat ttctcaaaat cttaaaaact ttctctcaat tctctctacc   3000
gtgatcaagg taaatttctg tgttccttat tctctcaaaa tcttcgattt tgttttcgtt   3060
cgatcccaat ttcgtatatg ttctttggtt tagattctgt taatcttaga tcgaagacga   3120
ttttctgggt ttgatcgtta gatatcatct taattctcga ttagggtttc atagatatca   3180
tccgatttgt tcaaataatt tgagttttgt cgaataatta ctcttcgatt tgtgatttct   3240
atctagatct ggtgttagtt tctagtttgt gcgatcgaat ttgtcgatta atctgagttt   3300
ttctgattaa cagcggccgg gatccacacg acaccatggc tattgaggtt aagcctatca   3360
acgcagagga tacctatgac cttaggcata gagtgctcag accaaaccag cctatcgaag   3420
cctgcatgtt tgagtctgac cttactagga gtgcatttca ccttggtgga ttctacggag   3480
gtaaactgat ttccgtggct tcattccacc aagctgagca ctctgaactt caaggtaaga   3540
agcagtacca gcttagaggt gtggctacct tggaaggtta tagagagcag aaggctggtt   3600
ccagtctcgt gaaacacgct gaagagattc tcagaaagag aggtgctgac atgatctggt   3660
gtaatgccag gacatctgct tcaggatact acaggaagtt gggattcagt gagcaaggag   3720
aggtgttcga tactcctcca gttggacctc acatcctgat gtataagagg atcacataac   3780
tagctagtca gttaacctag acttgtccat cttctggatt ggccaactta attaatgtat   3840
gaaataaaag gatgcacaca tagtgacatg ctaatcacta taatgtgggc atcaaagttg   3900
tgtgttatgt gtaattacta gttatctgaa taaaagagaa agagatcatc catatttctt   3960
atcctaaatg aatgtcacgt gtctttataa ttctttgatg aaccagatgc atttcattaa   4020
ccaaatccat atacatataa atattaatca tatataatta atatcaattg ggttagcaaa   4080
acaaatctag tctaggtgtg ttttgcgaat gcgacagtcc gtaacttgga ctaaacaaat   4140
tgacctaaaa acatgagcat aactaaaact cccatgtaat ggttaaacta taaccaacaa   4200
```

-continued

```
atctcaaact atgagatata acacaagaca tctttgagaa attctaaacc gtagaataat   4260

ctcttacaaa aaatactcca aactatggaa aaacaacact gagatattct aaactataga   4320

ataaatctca ggaaaagaat tagcccatgt gaaaggcaca aaccgttaac attactaaaa   4380

ccctcgaatt cttttgcact gatcacccga cgaaaaccca agaaaataaa ttagataaat   4440

aaaaaaaacc aaaaccctaa taaaaaaaca aaacctaact tcacgtgaat caacgtcgtc   4500

atccggatca tcttcaccgt cttcatcgtc aacaccaccg atgaacgcca tcaaagctct   4560

aaaattataa tgcggaagtt ttaatttcga tcccaaagaa tcgtctgctc tgataccatg   4620

taaagtataa tagaatataa tatattattg tgttgtattt gataagagaa tacaatatgc   4680

atatatatag tggtaacatt aacataatgt taacactaga taatgctaac tttcctaaac   4740

acttaatgta aatatgctaa gaatatcttg tgattaactt gctcttcaag tctttccttt   4800

tagtcttgag ggtcttcatg ggtttcacgg gcttcacaat ctaggtctgt aagatacata   4860

tcttccagtc caacatattt ctaatatgct gattcctgaa acacccggat gagtaatttt   4920

tagatgatac attgaaaatt ctaagtaagg atcgaacatt gagcaatttt aaaaattaag   4980

tcaaaactct tacagtagtt ttatagtcat atactgttta cgaacagttt tggtgttttt   5040

taattagttt tgccgaagtt tgtttctgct ttgagtgctg actcaacacc gttttggtgt   5100

tctttgctat tattaactct aagatttaag attgtttatg tttttttgtt gatacctctt   5160

ttatcttaaa atatttttg gtgtgtattc cattgaaagt ttaaagtaat ttgtataaaa   5220

ataacaaatt ctttcaaaca tgaattttaa aattttattt aaaattatat tatcgaattt   5280

taaagtacta ttaaatttaa tgttactaaa aatattttaa gttgtgagtt ttataagttt   5340

tttagtgcta cgtggagttt tttagttaaa attaaaaatc ttttatgatt ttaggtgaga   5400

ctctaagtgg tataacaaaa ttcatattaa attctttagt tcatctaaaa ctcattaagt   5460

tttatccctt atataaaaga atgagatata tgtaatatat aaaatgatta gtctttttgc   5520

aaaaaaagag taaatagtat ttcaagaaac gaaaattaat gttttatgga gtgcgatgaa   5580

caaaatgtaa catttataaa cttggttcca tgtcaaaaaa aatgtaaaaa cgtataaaaa   5640

ttcaattgat actttagcca ttcagcttag tgactactag ctagcatgcc aaaaagtggc   5700

aatacaaact tgaagtattg attaagagat cgagcgggga ctggaacaga aggaaagact   5760

ggagacaaat tgaacaaacg acaaataaaa cgagcaagaa attaattcat catgtcgcct   5820

gaacaaatgg caattcctct caagaagcag agaaagccca ctaaatctgt gttgggacac   5880

ttgtctgaaa ccaaaatctg gtcttcgaca taaaaacaat gcattactaa acttgtcctc   5940

taagccggct agatgaaagg aacaacatca ccactctgaa accttactac atcctcccga   6000

aggaaagtga accgtgaagc acaacaaacg aataaattcc tctacatgta attgctaaac   6060

gtgcaaatca aattcaggac aataagcaac accaaatata aaaatcaggg gagatgagat   6120

agcaagaatt gaggtcgaag agagttgaat ttacagggag cagagctcac acctcca      6177
```

```
<210> SEQ ID NO 12
<211> LENGTH: 20
<212> TYPE: DNA
<213> ORGANISM: Artificial Sequence
<220> FEATURE:
<223> OTHER INFORMATION: right flanking genomic/right border transgene
      (10nt/10nt)

<400> SEQUENCE: 12

ttgcgaatgc gacagtccgt                                                  20
```

-continued

<210> SEQ ID NO 13
<211> LENGTH: 20
<212> TYPE: DNA
<213> ORGANISM: Artificial Sequence
<220> FEATURE:
<223> OTHER INFORMATION: left flanking genomic/left border transgene
(10nt/10nt)

<400> SEQUENCE: 13
ttttcattag ttagatcagg 20

<210> SEQ ID NO 14
<211> LENGTH: 40
<212> TYPE: DNA
<213> ORGANISM: Artificial Sequence
<220> FEATURE:
<223> OTHER INFORMATION: right flanking genomic/right border transgene
(20nt/20nt)

<400> SEQUENCE: 14
taggtgtgtt ttgcgaatgc gacagtccgt aacttggact 40

<210> SEQ ID NO 15
<211> LENGTH: 40
<212> TYPE: DNA
<213> ORGANISM: Artificial Sequence
<220> FEATURE:
<223> OTHER INFORMATION: left flanking genomic/left border transgene
(20nt/20nt)

<400> SEQUENCE: 15
ctcattacag ttttcattag ttagatcagg atattcttgt 40

<210> SEQ ID NO 16
<211> LENGTH: 60
<212> TYPE: DNA
<213> ORGANISM: Artificial Sequence
<220> FEATURE:
<223> OTHER INFORMATION: right flanking genomic/left border transgene
(30nt/30nt)

<400> SEQUENCE: 16
aaatctagtc taggtgtgtt ttgcgaatgc gacagtccgt aacttggact aaacaaattg 60

<210> SEQ ID NO 17
<211> LENGTH: 60
<212> TYPE: DNA
<213> ORGANISM: Artificial Sequence
<220> FEATURE:
<223> OTHER INFORMATION: left flanking genomic/left border transgene
(30nt/30nt)

<400> SEQUENCE: 17
ctcttcatag ctcattacag ttttcattag ttagatcagg atattcttgt ttaagatgtt 60

<210> SEQ ID NO 18
<211> LENGTH: 4174
<212> TYPE: DNA
<213> ORGANISM: Artificial Sequence
<220> FEATURE:
<223> OTHER INFORMATION: compelete transgene/right flanking genomic

<400> SEQUENCE: 18
ttagatcagg atattcttgt ttaagatgtt gaactctatg gaggtttgta tgaactgatg 60
atctaggacc ggataagttc ccttcttcat agcgaactta ttcaaagaat gttttgtgta 120

-continued

```
tcattcttgt tacattgtta ttaatgaaaa aatattattg gtcattggac tgaacacgag    180
tgttaaatat ggaccaggcc ccaaataaga tccattgata tatgaattaa ataacaagaa    240
taaatcgagt caccaaacca cttgcctttt ttaacgagac ttgttcacca acttgataca    300
aaagtcatta tcctatgcaa atcaataatc atacaaaaat atccaataac actaaaaaat    360
taaaagaaat ggataatttc acaatatgtt atacgataaa gaagttactt ttccaagaaa    420
ttcactgatt ttataagccc acttgcatta gataaatggc aaaaaaaaac aaaaaggaaa    480
agaaataaag cacgaagaat tctagaaaat acgaaatacg cttcaatgca gtgggaccca    540
cggttcaatt attgccaatt ttcagctcca ccgtatattt aaaaaataaa acgataatgc    600
taaaaaaata taaatcgtaa cgatcgttaa atctcaacgg ctggatctta tgacgaccgt    660
tagaaattgt ggttgtcgac gagtcagtaa taaacggcgt caaagtggtt gcagccggca    720
cacacgagtc gtgtttatca actcaaagca caaatacttt tcctcaacct aaaaataagg    780
caattagcca aaaacaactt tgcgtgtaaa caacgctcaa tacacgtgtc attttattat    840
tagctattgc ttcaccgcct tagctttctc gtgacctagt cgtcctcgtc ttttcttctt    900
cttcttctat aaaacaatac ccaaagagct cttcttcttc acaattcaga tttcaatttc    960
tcaaaatctt aaaaactttc tctcaattct ctctaccgtg atcaaggtaa atttctgtgt   1020
tccttattct ctcaaaatct tcgattttgt tttcgttcga tcccaatttc gtatatgttc   1080
tttggtttag attctgttaa tcttagatcg aagacgattt tctgggtttg atcgttagat   1140
atcatcttaa ttctcgatta gggtttcata gatatcatcc gatttgttca aataatttga   1200
gttttgtcga ataattactc ttcgatttgt gatttctatc tagatctggt gttagtttct   1260
agtttgtgcg atcgaatttg tcgattaatc tgagtttttc tgattaacag cggccgggat   1320
ccacacgaca ccatggctat tgaggttaag cctatcaacg cagaggatac ctatgacctt   1380
aggcatagag tgctcagacc aaaccagcct atcgaagcct gcatgtttga gtctgacctt   1440
actaggagtg catttcacct tggtggattc tacggaggta aactgatttc cgtggcttca   1500
ttccaccaag ctgagcactc tgaacttcaa ggtaagaagc agtaccagct tagaggtgtg   1560
gctaccttgg aaggttatag agagcagaag gctggttcca gtctcgtgaa acacgctgaa   1620
gagattctca gaaagagagg tgctgacatg atctggtgta atgccaggac atctgcttca   1680
ggatactaca ggaagttggg attcagtgag caaggagagg tgttcgatac tcctccagtt   1740
ggacctcaca tcctgatgta taagaggatc acataactag ctagtcagtt aacctagact   1800
tgtccatctt ctggattggc caacttaatt aatgtatgaa ataaaaggat gcacacatag   1860
tgacatgcta atcactataa tgtgggcatc aaagttgtgt gttatgtgta attactagtt   1920
atctgaataa aagagaaaga gatcatccat atttcttatc ctaaatgaat gtcacgtgtc   1980
tttataattc tttgatgaac cagatgcatt tcattaacca aatccatata catataaata   2040
ttaatcatat ataattaata tcaattgggt tagcaaaaca aatctagtct aggtgtgttt   2100
tgcgaatgcg acagtccgta acttggacta aacaaattga cctaaaaaca tgagcataac   2160
taaaactccc atgtaatggt taaactataa ccaacaaatc tcaaactatg agatataaca   2220
caagacatct ttgagaaatt ctaaaccgta gaataatctc ttacaaaaaa tactccaaac   2280
tatggaaaaa caacactgag atattctaaa ctatagaata aatctcagga aaagaattag   2340
cccatgtgaa aggcacaaac cgttaacatt actaaaaccc tcgaattctt ttgcactgat   2400
cacccgacga aaacccaaga aaataaatta gataaataaa aaaaaccaaa accctaataa   2460
aaaaacaaaa cctaacttca cgtgaatcaa cgtcgtcatc cggatcatct tcaccgtctt   2520
```

catcgtcaac accaccgatg aacgccatca aagctctaaa attataatgc ggaagtttta 2580
atttcgatcc caaagaatcg tctgctctga taccatgtaa agtataatag aatataatat 2640
attattgtgt tgtatttgat aagagaatac aatatgcata tatatagtgg taacattaac 2700
ataatgttaa cactagataa tgctaacttt cctaaacact taatgtaaat atgctaagaa 2760
tatcttgtga ttaacttgct cttcaagtct ttccttttag tcttgagggt cttcatgggt 2820
ttcacgggct tcacaatcta ggtctgtaag atacatatct tccagtccaa catatttcta 2880
atatgctgat tcctgaaaca cccggatgag taatttttag atgatacatt gaaaattcta 2940
agtaaggatc gaacattgag caattttaaa aattaagtca aaactcttac agtagtttta 3000
tagtcatata ctgtttacga acagttttgg tgttttttaa ttagttttgc cgaagtttgt 3060
ttctgctttg agtgctgact caacaccgtt ttggtgttct ttgctattat taactctaag 3120
atttaagatt gtttatgttt ttttgttgat acctctttta tcttaaaata ttttttggtg 3180
tgtattccat tgaaagttta aagtaatttg tataaaaata acaaattctt tcaaacatga 3240
attttaaaat tttatttaaa attatattat cgaattttaa agtactatta aatttaatgt 3300
tactaaaaat attttaagtt gtgagtttta taagtttttt agtgctacgt ggagtttttt 3360
agttaaaatt aaaaatcttt tatgatttta ggtgagactc taagtggtat aacaaaattc 3420
atattaaatt ctttagttca tctaaaactc attaagtttt atcccttata taaaagaatg 3480
agatatatgt aatatataaa atgattagtc tttttgcaaa aaaagagtaa atagtatttc 3540
aagaaacgaa aattaatgtt ttatggagtg cgatgaacaa aatgtaacat ttataaactt 3600
ggttccatgt caaaaaaaat gtaaaaacgt ataaaaattc aattgatact ttagccattc 3660
agcttagtga ctactagcta gcatgccaaa aagtggcaat acaaacttga agtattgatt 3720
aagagatcga gcggggactg gaacagaagg aaagactgga gacaaattga acaaacgaca 3780
aataaaacga gcaagaaatt aattcatcat gtcgcctgaa caaatggcaa ttcctctcaa 3840
gaagcagaga aagcccacta aatctgtgtt gggacacttg tctgaaacca aaatctggtc 3900
ttcgacataa aaacaatgca ttactaaact tgtcctctaa gccggctaga tgaaaggaac 3960
aacatcacca ctctgaaacc ttactacatc ctcccgaagg aaagtgaacc gtgaagcaca 4020
acaaacgaat aaattcctct acatgtaatt gctaaacgtg caaatcaaat tcaggacaat 4080
aagcaacacc aaatataaaa atcaggggag atgagatagc aagaattgag gtcgaagaga 4140
gttgaattta cagggagcag agctcacacc tcca 4174

<210> SEQ ID NO 19
<211> LENGTH: 4112
<212> TYPE: DNA
<213> ORGANISM: Artificial Sequence
<220> FEATURE:
<223> OTHER INFORMATION: left flanking genomic/compelete transgene

<400> SEQUENCE: 19
ctttcctgtg actctgtcac gttcatagat ttgaagacca ctcaacacaa tgataataag 60
aggaaaaata tctacagaag tttatatcaa caattacaat tattatagag aaaaagataa 120
aaatagcact aaatcaagtt tttgttccca aactagcatt caaagtcaaa aatcacaaaa 180
ataacactaa atgttttatc aaaaatcaca aacttagggt ttagagttaa agggtggggt 240
ttaggattta gggtttaggg tttagggttt agagtttagg gtttagggtt tagattttag 300
ggtttagggt ttagggttta gggtttagag tttagggttt agggtttatg gtttagggtt 360

-continued

```
tagggtttag agttgagaaa tgaggttttg gggataagat ttcaaatttt gaaaaataaa    420
aaaattaaaa ttttcaaagg ataaacttag aaaggtgcta ttttggtcat tttagttttt    480
gagtgctatt tttgtgatat aaacttagaa atgtgctatt ttggagattt gtcatttatt    540
atattcaaaa gaacaaaaca ttatacaaaa cagataaata gacgacgatg atgatgtgga    600
aattcagacg gccaatactc actctgtctt tccagccata cactttaaga taagatgggc    660
cctacagtca tccaacctaa gccaataatc tcacgattct tatctaatct catctttcct    720
caccgttaga tcatattaca ctatcgatcc ccatgtcata tggtacaccg cgatacactt    780
gataacgaag tatccactct tgaaatacgc gaaaaccaca tactccgctt ccttccctct    840
cactgtcaca actcatcgtt ccaaaaaacc cactgtatca acctcgacga tggagtcacg    900
cgtgctgcta cgcgccacag tcaccggagt accgcaattg agacgaccga tcggtgcgat    960
ccaccgtcag gtcagcactg cgtcgtcgtt ctcggctttt aggttttcag ctccgatcgg   1020
atcagtcgga gagggaggga acctgatctc cggtcgtcag ctccgtccga ttctcctcct   1080
cgatagctcg ccggagaaga gagagattct caagccggtt agagccgccg ctggagattc   1140
agctgggtaa gcaatgaggt ccgtttctgg ctcacttggt gttgactcgt ttgactcgag   1200
tgatctgact cgtttatttg cagggaggcg aaggttggat tcctcgggaa gtatccgtgg   1260
ctcgtcaccg gattcttctt cttcatgtgg tacgtgtgtc cctcacgcgc ttttgcggct   1320
ttaccgccaa agtttgatag cgtggattta cggttttgac cccttgttga tttttattac   1380
aggtacttct tgaatgtgat tttcaacatc cttaataaga agatctataa ttacttcccc   1440
tatccctagt aagtaaaata catttaaatt gtttttgaca tatgaaaaaa tttacattta   1500
catacattga tatctagtct ttttgtatct ctatttgatc atctgtaaaa aaaaaaaaat   1560
catctgtaaa taattgtaaa ggttaattca ttatatttaa aagattcggt ttaatgttta   1620
tatatgatcg agaataatat agttttggtc caatttagag tcgaatctta ataatgttgt   1680
ggtatcaaga gaatccattg tgctggtcca attcagatat ggttttctgt tttttttattt   1740
aatattattt tttaaaatgt tgtataattt cgtttcagac gcaaacaaat tacacttttt   1800
cctttcaatt gaatatagca ttacataaaa atcaagagaa tccatttgtt cctaaacata   1860
aattaatttt tgttctgttt tcagttttgt ttcggctgtt cacttgttcg ttggagttgt   1920
ctactgcttg ctgagctggt ccgtgggcct tcctaaacgt gccgtaagtt cttctcttca   1980
tagctcatta cagttttcat tagttagatc aggatattct tgtttaagat gttgaactct   2040
atggaggttt gtatgaactg atgatctagg accggataag ttcccttctt catagcgaac   2100
ttattcaaag aatgttttgt gtatcattct tgttacattg ttattaatga aaaaatatta   2160
ttggtcattg gactgaacac gagtgttaaa tatggaccag gccccaaata agatccattg   2220
atatatgaat taaataacaa gaataaatcg agtcaccaaa ccacttgcct tttttaacga   2280
gacttgttca ccaacttgat acaaaagtca ttatcctatg caaatcaata atcatacaaa   2340
aatatccaat aacactaaaa aattaaaaga aatggataat ttcacaatat gttatacgat   2400
aaagaagtta cttttccaag aaattcactg attttataag cccacttgca ttagataaat   2460
ggcaaaaaaa aacaaaaagg aaaagaaata aagcacgaag aattctagaa aatacgaaat   2520
acgcttcaat gcagtgggac ccacggttca attattgcca attttcagct ccaccgtata   2580
tttaaaaaat aaaacgataa tgctaaaaaa atataaatcg taacgatcgt taaatctcaa   2640
cggctggatc ttatgacgac cgttagaaat tgtggttgtc gacgagtcag taataaacgg   2700
cgtcaaagtg gttgcagccg gcacacacga gtcgtgttta tcaactcaaa gcacaaatac   2760
```

ttttcctcaa cctaaaaata aggcaattag ccaaaaacaa ctttgcgtgt aaacaacgct 2820
caatacacgt gtcattttat tattagctat tgcttcaccg ccttagcttt ctcgtgacct 2880
agtcgtcctc gtcttttctt cttcttcttc tataaaacaa tacccaaaga gctcttcttc 2940
ttcacaattc agatttcaat ttctcaaaat cttaaaaact ttctctcaat tctctctacc 3000
gtgatcaagg taaatttctg tgttccttat tctctcaaaa tcttcgattt tgttttcgtt 3060
cgatcccaat ttcgtatatg ttctttggtt tagattctgt taatcttaga tcgaagacga 3120
ttttctgggt ttgatcgtta gatatcatct taattctcga ttagggtttc atagatatca 3180
tccgatttgt tcaaataatt tgagttttgt cgaataatta ctcttcgatt tgtgatttct 3240
atctagatct ggtgttagtt tctagtttgt gcgatcgaat ttgtcgatta atctgagttt 3300
ttctgattaa cagcggccgg gatccacacg acaccatggc tattgaggtt aagcctatca 3360
acgcagagga tacctatgac cttaggcata gagtgctcag accaaaccag cctatcgaag 3420
cctgcatgtt tgagtctgac cttactagga gtgcatttca ccttggtgga ttctacggag 3480
gtaaactgat ttccgtggct tcattccacc aagctgagca ctctgaactt caaggtaaga 3540
agcagtacca gcttagaggt gtggctacct tggaaggtta tagagagcag aaggctggtt 3600
ccagtctcgt gaaacacgct gaagagattc tcagaaagag aggtgctgac atgatctggt 3660
gtaatgccag gacatctgct tcaggatact acaggaagtt gggattcagt gagcaaggag 3720
aggtgttcga tactcctcca gttggacctc acatcctgat gtataagagg atcacataac 3780
tagctagtca gttaacctag acttgtccat cttctggatt ggccaactta attaatgtat 3840
gaaataaaag gatgcacaca tagtgacatg ctaatcacta taatgtgggc atcaaagttg 3900
tgtgttatgt gtaattacta gttatctgaa taaaagagaa agagatcatc catatttctt 3960
atcctaaatg aatgtcacgt gtctttataa ttctttgatg aaccagatgc atttcattaa 4020
ccaaatccat atacatataa atattaatca tatataatta atatcaattg ggttagcaaa 4080
acaaatctag tctaggtgtg ttttgcgaat gc 4112

<210> SEQ ID NO 20
<211> LENGTH: 27
<212> TYPE: DNA
<213> ORGANISM: Artificial Sequence
<220> FEATURE:
<223> OTHER INFORMATION: Primer 10-O-3514

<400> SEQUENCE: 20
ggtccgtggg ccttcctaaa cgtgccg 27

<210> SEQ ID NO 21
<211> LENGTH: 30
<212> TYPE: DNA
<213> ORGANISM: Artificial Sequence
<220> FEATURE:
<223> OTHER INFORMATION: Primer 09-O-2824

<400> SEQUENCE: 21
gttcttctct tcatagctca ttacagtttt 30

<210> SEQ ID NO 22
<211> LENGTH: 24
<212> TYPE: DNA
<213> ORGANISM: Artificial Sequence
<220> FEATURE:
<223> OTHER INFORMATION: Primer 09-O-3249

-continued

<400> SEQUENCE: 22
acagatgaag ttcgggacga gtac 24

<210> SEQ ID NO 23
<211> LENGTH: 37
<212> TYPE: DNA
<213> ORGANISM: Artificial Sequence
<220> FEATURE:
<223> OTHER INFORMATION: Primer 10-O-3515

<400> SEQUENCE: 23
ttatccggtc ctagatcatc agttcataca aacctcc 37

<210> SEQ ID NO 24
<211> LENGTH: 28
<212> TYPE: DNA
<213> ORGANISM: Artificial Sequence
<220> FEATURE:
<223> OTHER INFORMATION: Primer 09-O-2825

<400> SEQUENCE: 24
caaacctcca tagagttcaa catcttaa 28

<210> SEQ ID NO 25
<211> LENGTH: 27
<212> TYPE: DNA
<213> ORGANISM: Artificial Sequence
<220> FEATURE:
<223> OTHER INFORMATION: Primer 09-O-3251

<400> SEQUENCE: 25
caggttgaga tccacatgct taaatat 27

<210> SEQ ID NO 26
<211> LENGTH: 23
<212> TYPE: DNA
<213> ORGANISM: Artificial Sequence
<220> FEATURE:
<223> OTHER INFORMATION: Primer 09-QP83

<400> SEQUENCE: 26
ttagttagat caggatattc ttg 23

<210> SEQ ID NO 27
<211> LENGTH: 20
<212> TYPE: DNA
<213> ORGANISM: Artificial Sequence
<220> FEATURE:
<223> OTHER INFORMATION: Primer 09-QP87

<400> SEQUENCE: 27
aagaagaatc atcatgcttc 20

*BRASSICA* GAT EVENT AND COMPOSITIONS AND METHODS FOR THE IDENTIFICATION AND/OR DETECTION THEREOF

This application is a Continuation of U.S. application Ser. No. 14/047,452, filed Oct. 7, 2013, now allowed, which is a Divisional of U.S. application Ser. No. 12/953,852, filed Nov. 24, 2010, now U.S. Pat. No. 8,581,046, which claims the benefit of U.S. Provisional Application No. 61/309,385, filed Mar. 1, 2010, and U.S. Provisional Application No. 61/263,923, filed Nov. 24, 2009, the entire content which is hereby incorporated by reference.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 20150220_BB1875USCNT_SeqLst, a creation date of Feb. 20, 2015, and a size of 37 Kb. The sequence listing filed via EFS-Web is part of the specification and is hereby incorporated in its entirety by reference herein.

FIELD OF THE INVENTION

This invention is in the field of molecular biology. More specifically, this invention pertains to expression of a sequence that confers tolerance to glyphosate.

BACKGROUND OF THE INVENTION

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising, et al., (1988) *Ann. Rev. Genet* 22:421-477). At the same time the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. It is also observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into othergenetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants or for use in environmental monitoring, monitoring traits in crops in the field or monitoring products derived from a crop harvest, as well as for use in ensuring compliance of parties subject to regulatory or contractual terms.

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system would involve the use of crop plants which are tolerant to an herbicide so that when the herbicide was sprayed on a field of herbicide-tolerant crop plants, the crop plants would continue to thrive while non-herbicide-tolerant weeds were killed or severely damaged.

Due to local and regional variation in dominant weed species as well as preferred crop species, a continuing need exists for customized systems of crop protection and weed management which can be adapted to the needs of a particular region, geography, and/or locality. Method and compositions that allow for the rapid identification of events in plants that produce such qualities are needed. For example, a continuing need exists for methods of crop protection and weed management which can reduce the number of herbicide applications necessary to control weeds in a field, reduce the amount of herbicide necessary to control weeds in a field, reduce the amount of tilling necessary to produce a crop, and/or delay or prevent the development and/or appearance of herbicide-resistant weeds. A continuing need exists for methods and compositions of crop protection and weed management which allow the targeted use of a particular herbicide and for the efficient detection of such an event.

BRIEF SUMMARY OF THE INVENTION

Compositions and methods related to transgenic glyphosate-tolerant *Brassica* plants are provided. Specifically, the present invention provides *Brassica* plants containing a transgene which imparts tolerance to glyphosate. The event may be, for example, DP-073496-4. The *Brassica* plant harboring the transgene at the recited chromosomal location comprises unique genomic/transgene junctions having at least the polynucleotide sequence of SEQ ID NO: 2 or at least the polynucleotide sequence of SEQ ID NO: 12 and/or 13. Further provided are the seeds deposited as Patent Deposit Number PTA-11504 and plants, plant cells, plant parts, seed and plant products derived therefrom. Characterization of the genomic insertion site of DP-073496-4 or any other event comprising integration of the glyphosate-tolerance transgene provides for an enhanced breeding efficiency and enables the use of molecular markers to track the transgene insert in the breeding populations and progeny thereof. Various methods and compositions for the identification, detection, and use of the glyphosate-N-acetyltransferase ("GAT" or "glyat") transformation event in *Brassica* are provided.

BRIEF DESCRIPTION OF THE DRAWINGS

FIG. 1 shows synthesis of plasmid PHP28181. Plasmid PHP28181 was used to produce the GAT *Brassica* lines.

FIG. 2 provides a schematic map of plasmid PHP28181.

FIG. 3 provides a schematic map of insertion DNA, fragment PHP28181A.

FIG. 4 provides a schematic representation of fragment A from PHP28181 (PHP28181A), specifically a schematic map of Hind III/Not I fragment (PHP28181A) containing the gat4621 gene cassette that was used for plant transformation to generate DP-073496-4 *Brassica*. The fragment size is 2112 bp. The construct-specific primer locations of 09-0-3290/09-0-3288 are indicated on the map.

FIG. 5 Southern analysis of Construct Specific PCR of Leaf DNA From DP-073496-4 *Brassica* and Non-Genetically Modified Control *Brassica*. PCR amplification with primer set 09-0-3290/09-0-3288 targeting the unique ubiquitin promoter and gat4621 junction present in DP-073496-4canola. Expected PCR amplicon size is 675 bp.

FIG. 6 Southern analysis of *Brassica* FatA gene PCR of leaf DNA from DP-073496-4 *Brassica* and Non-Genetically Modified Control *Brassica*. PCR amplification of endogenous brassica FatA gene with primer set 09-0-2812/09-02813 as positive control for PCR amplification. Expected PCR amplicon size is 506 bp.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods related to transgenic glyphosate-tolerant *Brassica* plants are provided. Specifically, the present invention provides *Brassica* plants having event DP-073496-4 or another event comprising PHP28181A or an operable fragment or variant thereof. A *Brassica* plant having event DP-073496-4, for example, has been modified by the insertion of the glyphosate acetyltransferase (glyat4621) gene derived from *Bacillus licheniformis*. The glyat4621 gene was functionally improved by a gene shuffling process to optimize the kinetics of glyphosate acetyltransferase (GLYAT) activity for acetylating the herbicide glyphosate. The insertion of the glyat4621 gene in the plant confers tolerance to the herbicidal active ingredient glyphosate through the conversion of glyphosate to the non-toxic acetylated form. Thus, a *Brassica* plant having the event DP-073496-4 is tolerant to glyphosate.

The polynucleotides conferring the glyphosate tolerance are inserted at a specific position in the *Brassica* genome and thereby produce, for example, the DP-073496-4 event. A *Brassica* plant harboring the DP-073496-4 event at a specific chromosomal location comprises genomic/transgene junctions having a unique polynucleotide sequence exemplified by SEQ ID NO: 2 or at least the polynucleotide sequence of SEQ ID NO: 12 and/or 13; SEQ ID NO: 14 and/or 15; or SEQ ID NO: 16 and/or 17. The characterization of the genomic insertion site of either event provides for an enhanced breeding efficiency and enables the use of molecular markers to track the transgene insert in the breeding populations and progeny thereof. Various methods and compositions for the identification, detection, and use of the *Brassica* DP-073496-4 event are provided herein. In one embodiment, a brassica plant having in its genome in the following order: a polynucleotide comprising SEQ ID NO: 12, a polynucleotide encoding a glyphosate-N-acetyltransferase and a polynucleotide comprising SEQ ID NO: 13 is provided. The term "event DP-073496-4 specific" refers to a polynucleotide sequence which is suitable for discriminatively identifying event DP-073496-4 in plants, plant material, or in products such as, but not limited to, oil produced from the seeds, or food or feed products (fresh or processed) comprising, or derived from, plant material.

Compositions further include seed deposited as Patent Deposit Numbers PTA-11504 and plants, plant cells, and seed derived therefrom. Applicant(s) have made a deposit of at least 2500 seeds of *Brassica* event DP-073496-4 with the American Type Culture Collection (ATCC), Manassas, Va. 20110-2209 USA on Nov. 24, 2010 and the deposit will be maintained under the terms of the Budapest Treaty on the International Recognition of the Deposit of Microorganisms for the Purposes of Patent Procedure. Deposits are made merely as a convenience for those of skill in the art and are not an admission that a deposit is required under 35 U.S.C. §112. The seeds deposited with the ATCC are taken from the deposit maintained by Pioneer Hi-Bred International, Inc., 7250 NW 62$^{nd}$ Avenue, Johnston, Iowa 50131-1000. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit. The deposit of seed comprising *Brassica* event DP-073496-4 will be maintained in the ATCC depository, which is a public depository, for a period of 30 years or 5 years after the most recent request or for the enforceable life of the patent, whichever is longer and will be replaced if it becomes nonviable during that period. Additionally, Applicant(s) will have satisfied all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event DP-073496-4 under the Plant Variety Protection Act (7 USC §2321, et seq.). Unauthorized seed multiplication prohibited. The seed may be regulated.

As used herein, the term "*Brassica*" means any *Brassica* plant and includes all plant varieties that can be bred with *Brassica*. As used herein, the term plant includes plant cells, plant organs, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, stalks, roots, root tips, anthers, and the like. Mature seed produced may be used for food, feed, fuel or other commercial or industrial purposes or for purposes of growing or reproducing the species. Progeny, variants and mutants of the regenerated plants are also included within the scope of the invention, provided that these parts comprise a DP-073496-4 event.

A transgenic "event" is produced by transformation of plant cells with a heterologous DNA construct(s) including a nucleic acid expression cassette that comprises a transgene of interest, the regeneration of a population of plants from cells which each comprise the inserted transgene and selection of a particular plant characterized by insertion into a particular genome location. An event is characterized phenotypically by the expression of the transgene(s). At the genetic level, an event is part of the genetic makeup of a plant. The term "event" also refers to progeny, produced by a sexual outcross between the transformant and another variety, that include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant comprising the inserted DNA and flanking sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500 or 5000 base pairs or greater which is located either immediately upstream of and contiguous with, or immediately downstream of and contiguous with, the original foreign insert DNA molecule. Non-limiting examples of the flanking regions of the DP-073496-4 event comprise polynucleotide sequences that are set forth in SEQ ID NO: 2, 8 and/or 9 and variants and fragments thereof.

Transformation procedures leading to random integration of the foreign DNA will result in transformants containing different flanking regions characteristic of and unique for each transformant. When recombinant DNA is introduced into a plant through traditional crossing, its flanking regions will generally not be changed. Transformants will also contain unique junctions between a piece of heterologous insert DNA and genomic DNA or two pieces of genomic DNA or two pieces of heterologous DNA. A "junction" is a point where two specific DNA fragments join. For example, a junction exists where insert DNA joins flanking DNA. A junction point also exists in a transformed organism where two DNA fragments join together in a manner that is modified from that found in the native organism. As used herein, "junction DNA" refers to DNA that comprises a junction point. Non-limiting examples of junction DNA from the DP-073496-4 event are forth in SEQ ID NO: 2, 11, 12, 13, 14, 15, 16, 17, 18, and/or 19 or variants and fragments thereof.

A DP073496-4 plant can be bred by first sexually crossing a first parental *Brassica* plant grown from the transgenic DP-073496-4 *Brassica* plant (or progeny thereof derived from transformation with the expression cassettes of the embodiments of the present invention that confer herbicide tolerance) and a second parental *Brassica* plant that lacks the herbicide tolerance phenotype, thereby producing a plurality of first progeny plants and then selecting a first progeny plant that displays the desired herbicide tolerance and selfing the first progeny plant, thereby producing a plurality of second progeny plants and then selecting from the second progeny plants which display the desired herbicide tolerance. These steps can further include the back-crossing of the first herbicide tolerant progeny plant or the second herbicide tolerant progeny plant to the second parental *Brassica* plant or a third parental *Brassica* plant, thereby producing a *Brassica* plant that displays the desired herbicide tolerance. It is further recognized that assaying progeny for phenotype is not required. Various methods and compositions, as disclosed elsewhere herein, can be used to detect and/or identify the DP073496-4 or other event.

Two different transgenic plants can also be sexually crossed to produce offspring that contain two independently-segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos, ed., American Society of Agronomy, Madison Wis. (1987).

The term "germplasm" refers to an individual, a group of individuals or a clone representing a genotype, variety, species or culture or the genetic material thereof.

A "line" or "strain" is a group of individuals of identical parentage that are generally inbred to some degree and that are generally isogenic or near isogenic.

Inbred lines tend to be highly homogeneous, homozygous and reproducible. Many analytical methods are available to determine the homozygosity and phenotypic stability of inbred lines.

The phrase "hybrid plants" refers to plants which result from a cross between genetically different individuals.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

The term "introgression" refers to the transmission of a desired allele of a genetic locus from one genetic background to another. In one method, the desired alleles can be introgressed through a sexual cross between two parents, wherein at least one of the parents has the desired allele in its genome.

In some embodiments, the polynucleotides conferring the brassica DP-073496-4 event of the invention are engineered into a molecular stack. In other embodiments, the molecular stack further comprises at least one additional polynucleotide that confers tolerance to a second herbicide. In one embodiment, the sequence confers tolerance to glufosinate, and in a specific embodiment, the sequence comprises pat gene. In another embodiment, the additional polynucleotide provides tolerance to ALS-inhibitor herbicides.

In other embodiments, an event of the invention comprises one or more traits of interest, and in more specific embodiments, the plant is stacked with any combination of polynucleotide sequences of interest in order to create plants with a desired combination of traits. A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser, et al., (1986) *Gene* 48:109; Lee, et al., (2003) *Appl. Environ. Microbiol.* 69:4648-4657 (Vip3A); Galitzky, et al., (2001) *Acta Crystallogr. D. Biol. Crystallogr.* 57:1101-1109 (Cry3Bb1) and Herman, et al., (2004) *J. Agric. Food Chem.* 52:2726-2734 (Cry1F)), lectins (Van Damme, et al., (1994) *Plant Mol. Biol.* 24:825, pentin (described in U.S. Pat. No. 5,981,722), and the like. The combinations generated can also include multiple copies of any one of the polynucleotides of interest.

In some embodiments, an event of the invention may be stacked with other herbicide-tolerance traits to create a transgenic plant of the invention with further improved properties. Other herbicide-tolerance polynucleotides that could be used in such embodiments include those conferring tolerance to glyphosate by other modes of action, such as, for example, a gene that encodes a glyphosate oxido-reductase enzyme as described more fully in U.S. Pat. Nos. 5,776,760 and 5,463,175. Other traits that could be combined with an event of the invention include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and U.S. Pat. No. 5,491,288 and International Publication Numbers WO 97/04103; WO 00/66746; WO 01/66704 and WO 00/66747. Other traits that could be combined with the an event of the invention include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937 and 5,378,824 and International Publication Number WO 96/33270.

In some embodiments, an event of the invention may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268,549 and 6,069,115 and International Publication Number WO 99/23886. Other examples of suitable herbicide-tolerance traits that could be stacked with an event of the invention include aryloxyalkanoate dioxygenase polynucleotides (which reportedly confer tolerance to 2,4-D and other phenoxy auxin herbicides as well as to aryloxyphenoxypropionate herbicides as described, for example, in International Publication WO 05/107437) and dicamba-tolerance polynucleotides as described, for example, in Herman, et al., (2005) *J. Biol. Chem.* 280:24759-24767.

Other examples of herbicide-tolerance traits that could be combined with an event disclosed herein include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616 and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with an event disclosed herein include those conferred by polynucleotides conferring altered protoporphyrinogen oxidase (protox) activity, as described in U.S. Pat. Nos. 6,288,306 B1; 6,282,837 B1 and 5,767,373 and International Publication Number WO 01/12825. Plants containing such polynucleotides can exhibit improved tolerance to any of a variety of herbicides which target the protox enzyme (also referred to as "protox inhibitors").

In other embodiments, an ALS inhibitor-tolerant trait is combined with the event disclosed herein. As used herein, an "ALS inhibitor-tolerant polypeptide" comprises any polypeptide which when expressed in a plant confers tolerance to at least one ALS inhibitor. A variety of ALS inhibitors are known and include, for example, sulfonylurea, imidazolinone, triazolopyrimidines, pryimidinyoxy(thio)benzoates, and/or sulfonylaminocarbonyltriazolinone herbicide. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio) benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. In some embodiments, the ALS inhibitor-tolerant polynucleotides contain at least one nucleotide mutation resulting in one amino acid change in the ALS polypeptide. In specific embodiments, the change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. See also, SEQ ID NO:65 comprising a soybean HRA sequence; SEQ ID NO:66 comprising a maize HRA sequence; SEQ ID NO:67 comprising an *Arabidopsis* HRA sequence; and SEQ ID NO:86 comprising an HRA sequence used in cotton. The HRA mutation in ALS finds particular use in one embodiment of the invention. The mutation results in the production of an acetolactate synthase polypeptide which is resistant to at least one ALS inhibitor chemistry in comparison to the wild-type protein. For example, a plant expressing an ALS inhibitor-tolerant polypeptide may be tolerant of a dose of sulfonylurea, imidazolinone, triazolopyrimidines, pyrimidinyloxy(thio) benzoates, and/or sulfonylaminocarbonyltriazolinone herbicide that is at least 2, 3, 4, 5, 6, 7, 8, 9, 10, 15, 20, 25, 30, 35, 40, 50, 70, 80, 100, 125, 150, 200, 500, or 1000 times higher than a dose of the herbicide that would cause damage to an appropriate control plant. In some embodiments, an ALS inhibitor-tolerant polypeptide comprises a number of mutations. Additionally, plants having an ALS inhibitor polypeptide can be generated through the selection of naturally occurring mutations that impart tolerance to glyphosate.

In some embodiments, the ALS inhibitor-tolerant polypeptide confers tolerance to sulfonylurea and imidazolinone herbicides. Sulfonylurea and imidazolinone herbicides inhibit growth of higher plants by blocking acetolactate synthase (ALS), also known as, acetohydroxy acid synthase (AHAS). For example, plants containing particular mutations in ALS (e.g., the S4 and/or HRA mutations) are tolerant to sulfonylurea herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor-tolerant polypeptide comprises a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

Other examples of herbicide-tolerance traits that could be combined with an event disclosed herein include those conferring tolerance to at least one herbicide in a plant such as, for example, a brassica plant or horseweed. Herbicide-tolerant weeds are known in the art, as are plants that vary in their tolerance to particular herbicides. See, e.g., Green and Williams, (2004) "Correlation of Corn (*Zea mays*) Inbred Response to Nicosulfuron and Mesotrione," poster presented at the WSSA Annual Meeting in Kansas City, Mo., Feb. 9-12, 2004; Green, (1998) *Weed Technology* 12:474-477; Green and Ulrich, (1993) *Weed Science* 41:508-516. The trait(s) responsible for these tolerances can be combined by breeding or via other methods with an event disclosed herein to provide a plant of the invention as well as methods of use thereof.

An event disclosed herein can also be combined with at least one other trait to produce plants of the present invention that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802 and 5,703,409; U.S. Pat. No. 5,850,016); barley high lysine (Williamson, et al., (1987) *Eur. J. Biochem.* 165:99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer, et al., (2002) *Appl. Microbiol. Biotechnol.* 59:224-230) and OLCH (high oleic acid content; see, e.g., Fernandez-Moya, et al., (2005) *J. Agric. Food Chem.* 53:5326-5330).

An event disclosed herein may also be combined with other desirable traits such as, for example, fumonisin detoxification genes (U.S. Pat. No. 5,792,931), avirulence and disease resistance genes (Jones, et al., (1994) *Science* 266:789; Martin, et al., (1993) *Science* 262:1432; Mindrinos, et al., (1994) *Cell* 78:1089) and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)) and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see, U.S. Pat. No. 5,583,210), stalk strength, flowering time or transformation technology traits such as cell cycle regulation or gene targeting (e.g., WO 99/61619, WO 00/17364 and WO 99/25821), the disclosures of which are herein incorporated by reference.

In another embodiment, an event disclosed herein can also be combined with the Rcg1 sequence or biologically active variant or fragment thereof. The Rcg1 sequence is an anthracnose stalk rot resistance gene in corn. See, for example, U.S. patent application Ser. Nos. 11/397,153, 11/397,275 and 11/397,247, each of which is herein incorporated by reference.

These stacked combinations can be created by any method including, but not limited to, breeding plants by any conventional methodology or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855 and WO99/25853, all of which are herein incorporated by reference.

As used herein, the use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

A DP-073496-4 *Brassica* plant comprises an expression cassette having an optimized glyphosate acetyltransferase polynucleotide. The cassette can include 5' and 3' regulatory sequences operably linked to the glyat polynucleotides. "Operably linked" is intended to mean a functional linkage between two or more elements. For example, an operable linkage between a polynucleotide of interest and a regulatory sequence (i.e., a promoter) is functional link that allows for the expression of the polynucleotide of interest. Operably linked elements may be contiguous or non-contiguous. When used to refer to the joining of two protein coding regions, by operably linked it is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a coding region and a transcriptional and translational termination region functional in plants. "Promoter" refers to a nucleotide sequence capable of controlling the expression of a coding sequence or functional RNA. In general, a coding sequence is located 3' to a promoter sequence. The promoter sequence can comprise proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature or even comprise synthetic nucleotide segments. It is understood by those skilled in the art that different promoters may direct the expression of a gene in different tissues or cell types or at different stages of development or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, nucleic acid fragments of different lengths may have identical promoter activity.

The expression cassettes may also contain 5' leader sequences. Such leader sequences can act to enhance translation. The regulatory regions (i.e., promoters, transcriptional regulatory regions, RNA processing or stability regions, introns, polyadenylation signals, transcriptional termination regions and translational termination regions) and/or the coding region may be native/analogous or heterologous to the host cell or to each other.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster, (1995) *Mol. Biotechnol.* 3:225-236). The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, et al., (1989) *Plant Cell* 1:671-680.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. The expression cassette can also comprise a selectable marker gene for the selection of transformed cells. Selectable marker genes are utilized for the selection of transformed cells or tissues.

Isolated polynucleotides are provided that can be used in various methods for the detection and/or identification of the brassica DP-073496-4 event. An "isolated" or "purified" polynucleotide or biologically active portion thereof, is substantially or essentially free from components that normally accompany or interact with the polynucleotide as found in its naturally occurring environment. Thus, an isolated or purified polynucleotide is substantially free of other cellular material or culture medium when produced by recombinant techniques or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived.

In specific embodiments, the polynucleotides of the invention comprise the junction DNA sequence set forth in NO: 2, or variants and/or fragments thereof or the junction DNA sequence set forth in SEQ ID NO:12 and/or 13. In other embodiments, the polynucleotides of the invention comprise the junction DNA sequences set forth in SEQ ID NO: 14, 15, 16, 17, 18 and/or 19 or variants and fragments thereof. In specific embodiments, methods of detection described herein amplify a polynucleotide comprising a junction of the specific DP-073496-4 event. Fragments and variants of junction DNA sequences are suitable for discriminatively identifying either event DP-073496-4. As discussed elsewhere herein, such sequences find use as primers and/or probes.

In other embodiments, the polynucleotides of the invention comprise polynucleotides that can detect a DP-073496-4 event or a region specific to DP-073496-4.

Such sequences include any polynucleotide set forth in SEQ ID NO: 2, 4, 5, 6, 7, 8, 9, 10, 11, 12, 13, 14, 15, 16, 17, 18, 19, 20, 21, 22, 23, 24, 25, 26, 27 or variants and fragments thereof. Fragments and variants of polynucleotides that detect a DP-073496-4 event or a region specific to DP-073496-4 are suitable for discriminatively identifying event DP-073496-4. As discussed elsewhere herein, such sequences find use as primers and/or probes.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide and/or substitution of one or more nucleotides at one or more sites in the native polynucleotide.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide. In the case of the present invention, the probe is complementary to a strand of isolated DNA from *Brassica* event DP-073496-4, whether from a *Brassica* plant or from a sample that includes DNA from the event. Probes according to the present invention include not only deoxyribonucleic or ribonucleic acids but also polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159, herein incorporated by reference). Any combination of primers can be used such that the pair allows for the detection of a DP-073496-4 event or a region specific to DP-073496-4.

Probes and primers are of sufficient nucleotide length to bind to the target DNA sequence and specifically detect and/or identify a polynucleotide having a DP-073496-4 event. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more or between about 11-20, 20-30, 30-40, 40-50, 50-100, 100-200, 200-300, 300-400, 400-500, 500-600, 600-700, 700-800 or more nucleotides in length are used. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide, or can differ from the target sequence by 1, 2, 3, 4, 5, 6 or more nucleotides. Probes can be used as primers, but are generally designed to bind to the target DNA or RNA and are not used in an amplification process. In one non-limiting embodiment, a probe can comprises a polynucleotide encoding the glyat4621 sequence or any variant or fragment thereof.

Specific primers can be used to amplify an integration fragment to produce an amplicon that can be used as a "specific probe" or can itself be detected for identifying event DP-073496-4 in biological samples. Alternatively, a probe of the invention can be used during the PCR reaction to allow for the detection of the amplification event (i.e., a Taqman™ probe or an MGB probe, so called real-time PCR). When the probe is hybridized with the polynucleotides of a biological sample under conditions which allow for the binding of the probe to the sample, this binding can be detected and thus allow for an indication of the presence of event DP-073496-4 in the biological sample. Such identification of a bound probe has been described in the art. In an embodiment of the invention, the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95% and between 95 and 100% identical (or complementary) to a specific region of the DP-073496-4 event.

As used herein, "amplified DNA" or "amplicon" refers to the product of polynucleotide amplification of a target polynucleotide that is part of a nucleic acid template. For example, to determine whether a *Brassica* plant resulting from a sexual cross contains the DP-073496-4 event, DNA extracted from the *Brassica* plant tissue sample may be subjected to a polynucleotide amplification method using a DNA primer pair that includes a first primer derived from flanking sequence adjacent to the insertion site of inserted heterologous DNA and a second primer derived from the inserted heterologous DNA to produce an amplicon that is diagnostic for the presence of the DP-073496-4 event DNA. In specific embodiments, the amplicon comprises a DP-073496-4 junction polynucleotide (i.e., a portion of SEQ ID NO: 2 which spans the junction site, such as, for example, SEQ ID NO: 10, 11, 12, 13, 14, 15, 16, 17, 18 and/or 19 or variants and fragments thereof). By "diagnostic" for a DP-073496-4 event, the use of any method or assay which discriminates between the presence or the absence of a DP-073496-4 event in a biological sample is intended. Alternatively, the second primer may be derived from the flanking sequence. In still other embodiments, primer pairs can be derived from flanking sequence on both sides of the inserted DNA so as to produce an amplicon that includes the entire insert polynucleotide of the expression construct as well as the sequence flanking the transgenic insert. See, FIG. 3. The amplicon is of a length and has a sequence that is also diagnostic for the event (i.e., has a junction DNA from a DP-073496-4 event). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction or about twenty thousand nucleotide base pairs. The use of the term "amplicon" specifically excludes primer dimers that may be formed in the DNA thermal amplification reaction.

Methods for preparing and using probes and primers are described, for example, in *Molecular Cloning: A Laboratory Manual,* 2.sup.nd ed, vol. 1-3, ed. Sambrook, et al., Cold Spring Harbor Laboratory Press, Cold Spring Harbor, N.Y. 1989 (hereinafter, "Sambrook, et al., 1989"); *Current Protocols in Molecular Biology*, ed. Ausubel, et al., Greene Publishing and Wiley-Interscience, New York, 1992 (with periodic updates) (hereinafter, "Ausubel, et al., 1992") and Innis, et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

It is to be understood that as used herein the term "transgenic" includes any cell, cell line, callus, tissue, plant part or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere, et al., (1987) *Meth. Enzymol.* 143:277) and particle-accelerated or "gene gun" transformation technology (Klein, et al., (1987) *Nature* (London) 327:70-73; U.S. Pat. No. 4,945,050, incorporated herein by reference). Additional transformation methods are disclosed below.

Thus, isolated polynucleotides of the invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels, et al., (1985; Supp. 1987) *Cloning Vectors: A Laboratory Manual*, Weissbach and Weissbach, (1989) *Methods for Plant Molecular Biology* (Academic Press, New York) and Flevin, et al., (1990) *Plant Molecular Biology Manual* (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated or cell- or tissue-specific expression), a transcription initiation start site, a ribosome binding site, an RNA processing signal, a transcription termination site and/or a polyadenylation signal.

Various methods and compositions for identifying event DP-073496-4 are provided. Such methods find use in identifying and/or detecting a DP-073496-4 event in any biological material. Such methods include, for example, methods to confirm seed purity and methods for screening seeds in a seed lot for a DP-073496-4 event. In one embodiment, a method for identifying event DP-073496-4 in a biological sample is provided and comprises contacting the sample with a first and a second primer; and, amplifying a polynucleotide comprising a DP-073496-4 specific region.

A biological sample can comprise any sample in which one desires to determine if DNA having event DP-073496-4 is present. For example, a biological sample can comprise any plant material or material comprising or derived from a plant material such as, but not limited to, food or feed products. As used herein, "plant material" refers to material which is obtained or derived from a plant or plant part. In specific embodiments, the biological sample comprises a brassica tissue.

Primers and probes based on the flanking DNA and insert sequences disclosed herein can be used to confirm (and, if necessary, to correct) the disclosed sequences by conventional methods, e.g., by re-cloning and sequencing such sequences. The polynucleotide probes and primers of the present invention specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a DP-073496-4 specific region or the polynucleotide can be used as a probe that hybridizes under stringent conditions to a polynucleotide from a DP-073496-4 event. The level or degree of hybridization which allows for the specific detection of a DP-073496-4 event or a specific region of a DP-073496-4 event is sufficient to distinguish the polynucleotide with the DP-073496-4 specific region from a polynucleotide lacking this region and thereby allow for discriminately identifying a DP-073496-4 event. By "shares sufficient sequence identity or complentarity to allow for the amplification of a DP-073496-4 specific event" is intended the sequence shares at least 80%, 85%, 90%, 91%, 92%, 93%, 94%, 95%, 96%, 97%, 98%, 99% or 100% identity or complementarity to a fragment or across the full length of the polynucleotide from the DP-073496-4 specific region.

Regarding the amplification of a target polynucleotide (e.g., by PCR) using a particular amplification primer pair, "stringent conditions" are conditions that permit the primer pair to hybridize to the target polynucleotide to which one primer having the corresponding wild-type sequence (or its complement) and another primer having the corresponding DP-073496-4 inserted DNA sequence would bind and preferably to produce an identifiable amplification product (the amplicon) having a DP-073496-4 specific region in a DNA thermal amplification reaction. In a PCR approach, oligonucleotide primers can be designed for use in PCR reactions to amplify a DP-073496-4 specific region. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York) and Innis and Gelfand, eds. (1999) *PCR Methods Manual* (Academic Press, New York). Methods of amplification are further described in U.S. Pat. Nos. 4,683, 195, 4,683,202 and Chen, et al., (1994) *PNAS* 91:5695-5699. These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the DP-073496-4 event or a DP-073496-4 specific region. For example, the amplicon can be about 10, 50, 100, 200, 300, 500, 700, 100, 2000, 3000, 4000, 5000 nucleotides in length or longer.

In specific embodiments, the specific region of the DP-073496-4 event is detected.

Any primer can be employed in the methods of the invention that allows a DP-073496-4 specific region to be amplified and/or detected. For example, in specific embodiments, the first primer comprises a fragment of a polynucleotide of SEQ ID NO: 2 or 3, wherein the first or the second primer shares sufficient sequence identity or complementarity to the polynucleotide to amplify the DP-073496-4 specific region. The primer pair can comprise a fragment of SEQ ID NO: 2 or 3. In another embodiment, the primer pair comprises a first primer comprising a fragment of SEQ ID NO: 8 and a second primer comprising a fragment of SEQ ID NO: 9 or 10; or, alternatively, the primer pair comprises a first primer comprising a fragment of SEQ ID NO: 9 and the second primer comprises a fragment of SEQ ID NO: 8 or 10. The primers can be of any length sufficient to amplify a DP-073496-4 specific region including, for example, at least 6, 7, 8, 9, 10, 15, 20, 15 or 30 or about 7-10, 10-15, 15-20, 20-25, 25-30, 30-35, 35-40, 40-45 nucleotides or longer. Additional primer are also set forth herein in Table 11.

As discussed elsewhere herein, any method to PCR amplify the DP-073496-4 event or specific region can be employed, including for example, real time PCR. See, for example, Livak, et al., (1995a). Oligonucleotides with fluorescent dyes at opposite ends provide a quenched probe system for detecting PCR product and nucleic acid hybridization. PCR methods and Applications. 4:357-362; U.S. Pat. No. 5,538,848; U.S. Pat. No. 5,723,591; Applied Biosystems User Bulletin No. 2, "Relative Quantitation of Gene Expression," P/N 4303859 and Applied Biosystems User Bulletin No. 5, "Multiplex PCR with Taqman VIC probes," P/N 4306236, each of which is herein incorporated by reference.

Thus, in specific embodiments, a method of detecting the presence of brassica event DP-073496-4 or progeny thereof in a biological sample is provided. The method comprises (a) extracting a DNA sample from the biological sample; (b) providing a pair of DNA primer molecules targeting the insert and/or junction (c) providing DNA amplification reaction conditions; (d) performing the DNA amplification reaction, thereby producing a DNA amplicon molecule and (e) detecting the DNA amplicon molecule, wherein the detection of said DNA amplicon molecule in the DNA amplification reaction indicates the presence of *Brassica* event DP-073496-4. In order for a nucleic acid molecule to serve as a primer or probe it needs only be sufficiently complementary in sequence to be able to form a stable double-stranded structure under the particular solvent and salt concentrations employed.

In hybridization techniques, all or part of a polynucleotide that selectively hybridizes to a target polynucleotide having a DP-073496-4 specific event is employed. By "stringent conditions" or "stringent hybridization conditions" when referring to a polynucleotide probe conditions under which a probe will hybridize to its target sequence to a detectably greater degree than to other sequences (e.g., at least 2-fold over background) are intended. Regarding the amplification of a target polynucleotide (e.g., by PCR) using a particular amplification primer pair, "stringent conditions" are conditions that permit the primer pair to hybridize to the target polynucleotide to which one primer having the corresponding wild-type sequence and another primer having the corresponding DP-073496-4 inserted DNA sequence. Stringent conditions are sequence-dependent and will be variable in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen, (1993) *Laboratory Techniques in Biochemistry and Molecular Biology—Hybridization with Nucleic Acid Probes*, Part I, Chapter 2 (Elsevier, New York) and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.) and Haymes, et al., (1985) In: *Nucleic Acid Hybridization, a Practical Approach*, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Further provided are methods of detecting the presence of DNA corresponding to the DP-073496-4 event in a sample. In one embodiment, the method comprises (a) contacting the biological sample with a polynucleotide probe that hybridizes under stringent hybridization conditions with DNA from brassica event DP-073496-4 and specifically detects the DP-073496-4 event; (b) subjecting the sample and probe to stringent hybridization conditions and (c) detecting hybridization of the probe to the DNA, wherein detection of hybridization indicates the presence of the DP-073496-4 event.

Various methods can be used to detect the DP-073496-4 specific region or amplicon thereof, including, but not limited to, Genetic Bit Analysis (Nikiforov, et al., (1994) *Nucleic Acid Res.* 22:4167-4175) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be annealed to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization and single base extension.

Another detection method is the Pyrosequencing technique as described by Winge, ((2000) *Innov. Pharma. Tech.* 00:18-24). In this method, an oligonucleotide is designed that overlaps the adjacent DNA and insert DNA junction. The oligonucleotide is annealed to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization and single or multi-base extension.

Fluorescence Polarization as described by Chen, et al., ((1999) *Genome Res.* 9:492-498) is also a method that can be used to detect an amplicon of the invention. Using this method, an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al., ((1996) *Nature Biotech.* 14:303-308). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the method embodiments of the invention, more particularly, the identification and/or the detection of the DP-073496-4 event in biological samples. The kit of the invention can be used and its components can be specifically adjusted, for purposes of quality control (e.g. purity of seed lots), detection of event DP-073496-4 in plant material or material comprising or derived from plant material, such as but not limited to food or feed products.

In specific embodiments, a kit for identifying event DP-073496-4 in a biological sample is provided. The kit comprises a first and a second primer, wherein the first and second primer amplify a polynucleotide comprising a DP-073496-4 specific region. In further embodiments, the kit also comprises a polynucleotide for the detection of the DP-073496-4 specific region. The kit can comprise, for example, a first primer comprising a fragment of a polynucleotide of SEQ ID NO: 2, 3, 8, 9, or 10, wherein the first or the second primer shares sufficient sequence homology or complementarity and specificity to the polynucleotide to amplify said DP-073496-4 specific region. For example, in specific embodiments, the first primer comprises a fragment of a polynucleotide of SEQ ID NO: 2 or 3, wherein the first or the second primer shares sufficient sequence homology or complementarity to the polynucleotide to amplify the DP-073496-4 specific region. In other embodiments, the first primer comprises a fragment of a polynucleotide of SEQ ID NO: 8 and the second primer comprises a fragment of SEQ ID NO: 9 or 10, wherein the first or the second primer shares sufficient sequence homology or complementarity to the polynucleotide to amplify the DP061061-7 specific region. Alternatively, the first primer pair comprises SEQ ID NO:9 or a variant or fragment thereof and the second primer comprises SEQ ID NO: 8 or 10 or a variant or fragment thereof. In other embodiments, the primer pair can comprise a fragment of SEQ ID NO: 2 and a fragment of SEQ ID NO: 3. The primers can be of any length sufficient to amplify the DP-073496-4 region including, for example, at least 6, 7, 8, 9, 10, 15, 20, 15 or 30 or about 7-10, 10-15, 15-20, 20-25, 25-30, 30-35, 35-40, 40-45 nucleotides or longer. Further provided are DNA detection kits comprising at least one polynucleotide that can specifically detect a DP-073496-4 specific region or insert DNA, wherein said polynucleotide comprises at least one DNA molecule of a sufficient length of contiguous nucleotides homologous or complementary to SEQ ID NO: 2, 3, 4, 5, 6, 7, 8, 9, 10, 11, 12, 13, 14, 15, 16, 17, 18 19, 20, 21, 22, 23, 24, 25, 26, or 27.

In one embodiment, a kit for identifying event DP-073496-4 in a biological sample is provided. The kit comprises a first and a second primer, wherein said first and said second primer amplify a polynucleotide comprising a DP-073496-4 specific region. In further embodiments, the kit further comprises a polynucleotide for the detection of the DP-073496-4 specific region. Thus, in one non-limiting embodiment, the first primer comprises a first fragment of SEQ ID NO: 11 and the second primer comprises a second fragment of SEQ ID NO:11, wherein the first and the second primer flank the DP-073496-4 specific region and share sufficient sequence homology or complementarity to the polynucleotide to amplify said DP-073496-4 specific region. As such, a kit can therefore include a first primer comprising a fragment of SEQ ID NO:8 and a second primer comprising a fragment of SEQ ID NO:9; or a first or a second primer comprising at least 8 consecutive polynucleotides of SEQ ID NO: 11; or a first or a second primer comprising at least 8 consecutive polynucleotides of SEQ ID NO:8 or 9.

In further embodiments, methods are provided for detecting a glyphosate-N-acetyltranferase polypeptide comprising analysing brassica plant tissues using an immunoassay comprising a glyphosate-N-acetyltranferase polypeptide-specific antibody or antibodies. In other embodiments, methods for detecting the presence of a polynucleotide that encodes a glyphosate-N-acetyltranferase polypeptide are provide and comprise assaying brassica plant tissue using PCR amplification. Kits for employing such methods are further provided.

Any of the polynucleotides and fragments and variants thereof employed in the methods and compositions of the invention can share sequence identity to a region of the transgene insert of the DP-073496-4 event, a junction sequence of the DP-073496-4 event, or a region of the insert in combination with a region of the flanking sequence of the DP-073496-4 event. Methods to determine the relationship of various sequences are known. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 872264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65 and Pearson, et al., (1994) *Meth. Mol. Biol.*

24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2 and the BLOSUM62 scoring matrix or any equivalent program thereof. By "equivalent program" any sequence comparison program that, for any two sequences in question, generates an alignment having identical nucleotide or amino acid residue matches and an identical percent sequence identity when compared to the corresponding alignment generated by GAP Version 10 is intended.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff, (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The present invention provides methods for controlling weeds in an area of cultivation, preventing the development or the appearance of herbicide resistant weeds in an area of cultivation, producing a crop and increasing crop safety. The term "controlling," and derivations thereof, for example, as in "controlling weeds" refers to one or more of inhibiting the growth, germination, reproduction and/or proliferation of and/or killing, removing, destroying or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The methods of the invention comprise planting the area of cultivation with the *Brassica* DP-073496-4 seeds or plants, and in specific embodiments, applying to the crop, seed, weed or area of cultivation thereof an effective amount of a herbicide of interest. It is recognized that the herbicide can be applied before or after the crop is planted in the area of cultivation. Such herbicide applications can include an application of glyphosate.

In one embodiment, the method of controlling weeds comprises planting the area with the DP-073496-4 *Brassica* seeds or plants and applying to the crop, crop part, seed of said crop or the area under cultivation, an effective amount of a herbicide, wherein said effective amount comprises an amount that is not tolerated by a second control crop when applied to the second crop, crop part, seed or the area of cultivation, wherein said second control crop does not express the GLYAT polynucleotide.

In another embodiment, the method of controlling weeds comprises planting the area with a DP-073496-4 *Brassica* crop seed or plant and applying to the crop, crop part, seed of said crop or the area under cultivation, an effective amount of a glyphosate herbicide, wherein said effective amount comprises a level that is above the recommended label use rate for the crop, wherein said effective amount is tolerated when applied to the DP-073496-4 *Brassica* crop, crop part, seed or the area of cultivation thereof.

A "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green, (1998) *Weed Technology* 12:474-477; Green and Ulrich, (1993) *Weed Science* 41:508-516. In other embodiments, the null segregant can be used as a control, as they are genetically identical to DP-073496-4 with the exception of the transgenic insert DNA.

Classification of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith, (1997) *Weed Technology* 11:384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application) or by how they are taken up by or affect the plant. For example, thifensulfuron-methyl and tribenuron-methyl are applied to the foliage of a crop and are generally metabolized there, while rimsulfuron and chlorimuron-ethyl are generally taken up through both the roots and foliage of a plant. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1).

Often, a herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments of the invention, a transgenic plant of the invention is tolerant to more than one herbicide or chemical in the same class or subclass, such as, for example, an inhibitor of PPO, a sulfonylurea or a synthetic auxin.

Typically, the plants of the present invention can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

The invention thereby provides a transgenic brassica plant which can be selected for use in crop production based on the prevalence of herbicide-tolerant weed species in the area where the transgenic crop is to be grown. Methods are known in the art for assessing the herbicide tolerance of various weed species. Weed management techniques are also known in the art, such as for example, crop rotation using a crop that is tolerant to a herbicide to which the local weed species are not tolerant. A number of entities monitor and publicly report the incidence and characteristics of herbicide-tolerant weeds, including the Herbicide Resistance Action Committee (HRAC), the Weed Science Society of America and various state agencies (see, for example, herbicide tolerance scores for various broadleaf weeds from the 2004 Illinois Agricultural Pest Management Handbook) and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler, (2004), 2005 *Herbicide Manual for Agricultural Professionals*, Pub. WC 92 Revised (Iowa State University Extension, Iowa State University of Science and Technology, Ames, Iowa); *Weed Control for Corn, Brassicas, and Sorghum*, Chapter 2 of "2004 Illinois Agricultural Pest Management Handbook" (University of Illinois Extension, University of Illinois at Urbana-Champaign, Ill.); *Weed Control Guide for Field Crops,* MSU Extension Bulletin E434 (Michigan State University, East Lansing, Mich.)).

TABLE 1

| Abbreviated version of HRAC Herbicide Classification |
|---|
| I. ALS Inhibitors (WSSA Group 2) |
| A. Sulfonylureas |
| 1. Azimsulfuron |
| 2. Chlorimuron-ethyl |
| 3. Metsulfuron-methyl |
| 4. Nicosulfuron |
| 5. Rimsulfuron |
| 6. Sulfometuron-methyl |
| 7. Thifensulfuron-methyl |
| 8. Tribenuron-methyl |
| 9. Amidosulfuron |
| 10. Bensulfuron-methyl |
| 11. Chlorsulfuron |
| 12. Cinosulfuron |
| 13. Cyclosulfamuron |
| 14. Ethametsulfuron-methyl |
| 15. Ethoxysulfuron |
| 16. Flazasulfuron |
| 17. Flupyrsulfuron-methyl |
| 18. Foramsulfuron |
| 19. Imazosulfuron |
| 20. Iodosulfuron-methyl |
| 21. Mesosulfuron-methyl |
| 22. Oxasulfuron |
| 23. Primisulfuron-methyl |
| 24. Prosulfuron |
| 25. Pyrazosulfuron-ethyl |
| 26. Sulfosulfuron |
| 27. Triasulfuron |
| 28. Trifloxysulfuron |
| 29. Triflusulfuron-methyl |
| 30. Tritosulfuron |
| 31. Halosulfuron-methyl |
| 32. Flucetosulfuron |
| B. Sulfonylaminocarbonyltriazolinones |
| 1. Flucarbazone |
| 2. Procarbazone |
| C. Triazolopyrimidines |
| 1. Cloransulam-methyl |
| 2. Flumetsulam |
| 3. Diclosulam |
| 4. Florasulam |
| 5. Metosulam |
| 6. Penoxsulam |
| 7. Pyroxsulam |
| D. Pyrimidinyloxy(thio)benzoates |
| 1. Bispyribac |
| 2. Pyriftalid |
| 3. Pyribenzoxim |
| 4. Pyrithiobac |
| 5. Pyriminobac-methyl |
| E. Imidazolinones |
| 1. Imazapyr |
| 2. Imazethapyr |
| 3. Imazaquin |
| 4. Imazapic |
| 5. Imazamethabenz-methyl |
| 6. Imazamox |
| II. Other Herbicides--Active Ingredients/ Additional Modes of Action |
| A. Inhibitors of Acetyl CoA carboxylase (ACCase) (WSSA Group 1) |
| 1. Aryloxyphenoxypropionates ('FOPs') |
| a. Quizalofop-P-ethyl |
| b. Diclofop-methyl |
| c. Clodinafop-propargyl |
| d. Fenoxaprop-P-ethyl |
| e. Fluazifop-P-butyl |
| f. Propaquizafop |
| g. Haloxyfop-P-methyl |
| h. Cyhalofop-butyl |
| i. Quizalofop-P-ethyl |
| 2. Cyclohexanediones ('DIMs') |
| a. Alloxydim |
| b. Butroxydim |
| c. Clethodim |
| d. Cycloxydim |
| e. Sethoxydim |

TABLE 1-continued

| Abbreviated version of HRAC Herbicide Classification |
|---|
| f. Tepraloxydim |
| g. Tralkoxydim |
| B. Inhibitors of Photosystem II-HRAC Group C1/WSSA Group 5 |
| 1. Triazines |
| a. Ametryne |
| b. Atrazine |
| c. Cyanazine |
| d. Desmetryne |
| e. Dimethametryne |
| f. Prometon |
| g. Prometryne |
| h. Propazine |
| i. Simazine |
| j. Simetryne |
| k. Terbumeton |
| l. Terbuthylazine |
| m. Terbutryne |
| n. Trietazine |
| 2. Triazinones |
| a. Hexazinone |
| b. Metribuzin |
| c. Metamitron |
| 3. Triazolinone |
| a. Amicarbazone |
| 4. Uracils |
| a. Bromacil |
| b. Lenacil |
| c. Terbacil |
| 5. Pyridazinones |
| a. Pyrazon |
| 6. Phenyl carbamates |
| a. Desmedipham |
| b. Phenmedipham |
| C. Inhibitors of Photosystem II--HRAC Group C2/WSSA Group 7 |
| 1. Ureas |
| a. Fluometuron |
| b. Linuron |
| c. Chlorobromuron |
| d. Chlorotoluron |
| e. Chloroxuron |
| f. Dimefuron |
| g. Diuron |
| h. Ethidimuron |
| i. Fenuron |
| j. Isoproturon |
| k. Isouron |
| l. Methabenzthiazuron |
| m. Metobromuron |
| n. Metoxuron |
| o. Monolinuron |
| p. Neburon |
| q. Siduron |
| r. Tebuthiuron |
| 2. Amides |
| a. Propanil |
| b. Pentanochlor |
| D. Inhibitors of Photosystem II--HRAC Group C3/WSSA Group 6 |
| 1. Nitriles |
| a. Bromofenoxim |
| b. Bromoxynil |
| c. Ioxynil |
| 2. Benzothiadiazinone (Bentazon) |
| a. Bentazon |
| 3. Phenylpyridazines |
| a. Pyridate |
| b. Pyridafol |
| E. Photosystem-I-electron diversion (Bipyridyliums) (WSSA Group 22) |
| 1. Diquat |
| 2. Paraquat |
| F. Inhibitors of PPO (protoporphyrinogen oxidase) (WSSA Group 14) |
| 1. Diphenylethers |
| a. Acifluorfen-Na |
| b. Bifenox |

TABLE 1-continued

| Abbreviated version of HRAC Herbicide Classification |
| --- |
| c. Chlomethoxyfen |
| d. Fluoroglycofen-ethyl |
| e. Fomesafen |
| f. Halosafen |
| g. Lactofen |
| h. Oxyfluorfen |
| 2. Phenylpyrazoles |
| a. Fluazolate |
| b. Pyraflufen-ethyl |
| 3. N-phenylphthalimides |
| a. Cinidon-ethyl |
| b. Flumioxazin |
| c. Flumiclorac-pentyl |
| 4. Thiadiazoles |
| a. Fluthiacet-methyl |
| b. Thidiazimin |
| 5. Oxadiazoles |
| a. Oxadiazon |
| b. Oxadiargyl |
| 6. Triazolinones |
| a. Carfentrazone-ethyl |
| b. Sulfentrazone |
| 7. Oxazolidinediones |
| a. Pentoxazone |
| 8. Pyrimidindiones |
| a. Benzfendizone |
| b. Butafenicil |
| 9. Others |
| a. Pyrazogyl |
| b. Profluazol |
| G. Bleaching: Inhibition of carotenoid biosynthesis at the phytoene desaturase step (PDS) (WSSA Group 12) |
| 1. Pyridazinones |
| a. Norflurazon |
| 2. Pyridinecarboxamides |
| a. Diflufenican |
| b. Picolinafen |
| 3. Others |
| a. Beflubutamid |
| b. Fluridone |
| c. Flurochloridone |
| d. Flurtamone |
| H. Bleaching: Inhibition of 4-hydroxyphenyl-pyruvate-dioxygenase (4-HPPD) (WSSA Group 28) |
| 1. Triketones |
| a. Mesotrione |
| b. Sulcotrione |
| c. topramezone |
| d. tembotrione |
| 2. Isoxazoles |
| a. Isoxachlortole |
| b. Isoxaflutole |
| 3. Pyrazoles |
| a. Benzofenap |
| b. Pyrazoxyfen |
| c. Pyrazolynate |
| 4. Others |
| a. Benzobicyclon |
| I. Bleaching: Inhibition of carotenoid biosynthesis (unknown target) (WSSA Group 11 and 13) |
| 1. Triazoles (WSSA Group 11) |
| a. Amitrole |
| 2. Isoxazolidinones (WSSA Group 13) |
| a. Clomazone |
| 3. Ureas |
| a. Fluometuron |
| 3. Diphenylether |
| a. Aclonifen |
| J. Inhibition of EPSP Synthase |
| 1. Glycines (WSSA Group 9) |
| a. Glyphosate |
| b. Sulfosate |
| K. Inhibition of glutamine synthetase |
| 1. Phosphinic Acids |
| a. Glufosinate-ammonium |

TABLE 1-continued

| Abbreviated version of HRAC Herbicide Classification |
| --- |
| b. Bialaphos |
| L. Inhibition of DHP (dihydropteroate) synthase (WSSA Group 18) |
| 1 Carbamates |
| a. Asulam |
| M. Microtubule Assembly Inhibition (WSSA Group 3) |
| 1. Dinitroanilines |
| a. Benfluralin |
| b. Butralin |
| c. Dinitramine |
| d. Ethalfluralin |
| e. Oryzalin |
| f. Pendimethalin |
| g. Trifluralin |
| 2. Phosphoroamidates |
| a. Amiprophos-methyl |
| b. Butamiphos |
| 3. Pyridines |
| a. Dithiopyr |
| b. Thiazopyr |
| 4. Benzamides |
| a. Pronamide |
| b. Tebutam |
| 5. Benzenedicarboxylic acids |
| a. Chlorthal-dimethyl |
| N. Inhibition of mitosis/microtubule organization WSSA Group 23) |
| 1. Carbamates |
| a. Chlorpropham |
| b. Propham |
| c. Carbetamide |
| O. Inhibition of cell division (Inhibition of very long chain fatty acids as proposed mechanism; WSSA Group 15) |
| 1. Chloroacetamides |
| a. Acetochlor |
| b. Alachlor |
| c. Butachlor |
| d. Dimethachlor |
| e. Dimethanamid |
| f. Metazachlor |
| g. Metolachlor |
| h. Pethoxamid |
| i. Pretilachlor |
| j. Propachlor |
| k. Propisochlor |
| l. Thenylchlor |
| 2. Acetamides |
| a. Diphenamid |
| b. Napropamide |
| c. Naproanilide |
| 3. Oxyacetamides |
| a. Flufenacet |
| b. Mefenacet |
| 4. Tetrazolinones |
| a. Fentrazamide |
| 5. Others |
| a. Anilofos |
| b. Cafenstrole |
| c. Indanofan |
| d. Piperophos |
| P. Inhibition of cell wall (cellulose) synthesis |
| 1. Nitriles (WSSA Group 20) |
| a. Dichlobenil |
| b. Chlorthiamid |
| 2. Benzamides (isoxaben (WSSA Group 21)) |
| a. Isoxaben |
| 3. Triazolocarboxamides (flupoxam) |
| a. Flupoxam |
| Q. Uncoupling (membrane disruption): (WSSA Group 24) |
| 1. Dinitrophenols |
| a. DNOC |
| b. Dinoseb |
| c. Dinoterb |

TABLE 1-continued

| Abbreviated version of HRAC Herbicide Classification |
| --- |
| R. Inhibition of Lipid Synthesis by other than ACC inhibition |
| 1. Thiocarbamates (WSSA Group 8) |
| a. Butylate |
| b. Cycloate |
| c. Dimepiperate |
| d. EPTC |
| e. Esprocarb |
| f. Molinate |
| g. Orbencarb |
| h. Pebulate |
| i. Prosulfocarb |
| j. Benthiocarb |
| k. Tiocarbazil |
| l. Triallate |
| m. Vernolate |
| 2. Phosphorodithioates |
| a. Bensulide |
| 3. Benzofurans |
| a. Benfuresate |
| b. Ethofumesate |
| 4. Halogenated alkanoic acids (WSSA Group 26) |
| a. TCA |
| b. Dalapon |
| c. Flupropanate |
| S. Synthetic auxins (IAA-like) (WSSA Group 4) |
| 1. Phenoxycarboxylic acids |
| a. Clomeprop |
| b. 2,4-D |
| c. Mecoprop |
| 2. Benzoic acids |
| a. Dicamba |
| b. Chloramben |
| c. TBA |
| 3. Pyridine carboxylic acids |
| a. Clopyralid |
| b. Fluroxypyr |
| c. Picloram |
| d. Tricyclopyr |
| 4. Quinoline carboxylic acids |
| a. Quinclorac |
| b. Quinmerac |
| 5. Others (benazolin-ethyl) |
| a. Benazolin-ethyl |
| T. Inhibition of Auxin Transport |
| 1. Phthalamates; semicarbazones (WSSA Group 19) |
| a. Naptalam |
| b. Diflufenzopyr-Na |
| U. Other Mechanism of Action |
| 1. Arylaminopropionic acids |
| a. Flamprop-M-methyl/-isopropyl |
| 2. Pyrazolium |
| a. Difenzoquat |
| 3. Organoarsenicals |
| a. DSMA |
| b. MSMA |
| 4. Others |
| a. Bromobutide |
| b. Cinmethylin |
| c. Cumyluron |
| d. Dazomet |
| e. Daimuron-methyl |
| f. Dimuron |
| g. Etobenzanid |
| h. Fosamine |
| i. Metam |
| j. Oxaziclomefone |
| k. Oleic acid |
| l. Pelargonic acid |
| m. Pyributicarb |

In certain methods, glyphosate, alone or in combination with another herbicide of interest, can be applied to the DP-073496-4 *Brassica* plants or their area of cultivation. Non-limiting examples of glyphosate formations are set forth in Table 2. In specific embodiments, the glyphosate is in the form of a salt, such as, ammonium, isopropylammonium, potassium, sodium (including sesquisodium) or trimesium (alternatively named sulfosate).

TABLE 2

Glyphosate formulations comparisons.

| Herbicide by Registered Trademark | Manufactuer | Salt | Active ingredient per gallon | Acid equivalent per gallon | Apply: fl oz/ acre | Acid equivalent per acre |
| --- | --- | --- | --- | --- | --- | --- |
| Roundup Original | Monsanto | Isopropylamine | 4 | 3 | 32 | 0.750 |
| Roundup Original II | Monsanto | Isopropylamine | 4 | 3 | 32 | 0.750 |
| Roundup Original MAX | Monsanto | Potassium | 5.5 | 4.5 | 22 | 0.773 |
| Roundup UltraMax | Monsanto | Isopropylamine | 5 | 3.68 | 26 | 0.748 |
| Roundup UltraMax II | Monsanto | Potassium | 5.5 | 4.5 | 22 | 0.773 |
| Roundup Weathermax | Monsanto | Potassium | 5.5 | 4.5 | 22 | 0.773 |
| Touchdown | Syngenta | Diammonium | 3.7 | 3 | 32 | 0.750 |
| Touchdown HiTech | Syngenta | Potassium | 6.16 | 5 | 20 | 0.781 |
| Touchdown Total | Syngenta | Potassium | 5.14 | 4.17 | 24 | 0.782 |
| Durango | Dow AgroSciences | Isopropylamine | 5.4 | 4 | 24 | 0.750 |
| Glyphomax | Dow AgroSciences | Isopropylamine | 4 | 3 | 32 | 0.750 |
| Glyphomax Plus | Dow AgroSciences | Isopropylamine | 4 | 3 | 32 | 0.750 |
| Glyphomax XRT | Dow AgroSciences | Isopropylamine | 4 | 3 | 32 | 0.750 |
| Gly Star Plus | Albaugh/Agri Star | Isopropylamine | 4 | 3 | 32 | 0.750 |
| Gly Star 5 | Albaugh/Agri Star | Isopropylamine | 5.4 | 4 | 24 | 0.750 |
| Gly Star Original | Albaugh/Agri Star | Isopropylamine | 4 | 3 | 32 | 0.750 |
| Gly-Flo | Micro Flo | Isopropylamine | 4 | 3 | 32 | 0.750 |
| Credit | Nufarm | Isopropylamine | 4 | 3 | 32 | 0.750 |
| Credit Extra | Nufarm | Isopropylamine | 4 | 3 | 32 | 0.750 |
| Credit Duo | Nufarm | Isopro. + monoamm. | 4 | 3 | 32 | 0.750 |
| Credit Duo Extra | Nufarm | Isopro. + monoamm. | 4 | 3 | 32 | 0.750 |

TABLE 2-continued

Glyphosate formulations comparisons.

| Herbicide by Registered Trademark | Manufactuer | Salt | Active ingredient per gallon | Acid equivalent per gallon | Apply: fl oz/ acre | Acid equivalent per acre |
|---|---|---|---|---|---|---|
| Extra Credit 5 | Nufarm | Isopropylamine | 5 | 3.68 | 26 | 0.748 |
| Cornerstone | Agriliance | Isopropylamine | 4 | 3 | 32 | 0.750 |
| Cornerstone Plus | Agriliance | Isopropylamine | 4 | 3 | 32 | 0.750 |
| Glyfos | Cheminova | Isopropylamine | 4 | 3 | 32 | 0.750 |
| Glyfos X-TRA | Cheminova | Isopropylamine | 4 | 3 | 32 | 0.750 |
| Rattler | Helena | Isopropylamine | 4 | 3 | 32 | 0.750 |
| Rattler Plus | Helena | Isopropylamine | 4 | 3 | 32 | 0.750 |
| Mirage | UAP | Isopropylamine | 4 | 3 | 32 | 0.750 |
| Mirage Plus | UAP | Isopropylamine | 4 | 3 | 32 | 0.750 |
| Glyphosate 41% | Helm Agro USA | Isopropylamine | 4 | 3 | 32 | 0.750 |
| Buccaneer | Tenkoz | Isopropylamine | 4 | 3 | 32 | 0.750 |
| Buccaneer Plus | Tenkoz | Isopropylamine | 4 | 3 | 32 | 0.750 |
| Honcho | Monsanto | Isopropylamine | 4 | 3 | 32 | 0.750 |
| Honcho Plus | Monsanto | Isopropylamine | 4 | 3 | 32 | 0.750 |
| Gly-4 | Univ. Crop Prot. Alli | Isopropylamine | 4 | 3 | 32 | 0.750 |
| Gly-4 Plus | Univ. Corp Prot. Alli | Isopropylamme | 4 | 3 | 32 | 0.750 |
| ClearOut 41 | Chemical Products Tech. | Isopropylamine | 4 | 3 | 32 | 0.750 |
| ClearOut 41 Plus | Chemical Products Tech. | Isopropylamine | 4 | 3 | 32 | 0.750 |
| Spitfire | Control Solutions | Isopropylamine | 4 | 3 | 32 | 0.750 |
| Spitfire Plus | Control Solutions | Isopropylamine | 4 | 3 | 32 | 0.750 |
| Glyphosate 4 | FarmerSaver.com | Isopropylamine | 4 | 3 | 32 | 0.750 |
| FS Glyphosate Plus | Growmark | Isopropylamine | 4 | 3 | 32 | 0.750 |
| Glyphosate Original | Griffin, LLC | Isopropylamine | 4 | 3 | 32 | 0.750 |

Thus, in some embodiments, a transgenic plant of the invention is used in a method of growing a DP-073496-4 brassica crop by the application of herbicides to which the plant is tolerant. In this manner, treatment with a combination of one of more herbicides which include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl) oxy]phenyl](3-fluorobenzoyl)amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metholachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate is disclosed.

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. and Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Combinations of various herbicides can result in a greater-than-additive (i.e., synergistic) effect on weeds and/or a less-than-additive effect (i.e., safening) on crops or other desirable plants. In certain instances, combinations of glyphosate with other herbicides having a similar spectrum of control but a different mode of action will be particularly advantageous for preventing the development of resistant weeds. Herbicidally effective amounts of any particular herbicide can be easily determined by one skilled in the art through simple experimentation.

Herbicides may be classified into groups and/or subgroups as described herein above with reference to their mode of action, or they may be classified into groups and/or subgroups in accordance with their chemical structure.

Sulfonamide herbicides have as an essential molecular structure feature a sulfonamide moiety ($—S(O)_2NH—$). As referred to herein, sulfonamide herbicides particularly comprise sulfonylurea herbicides, sulfonylaminocarbonyltriazolinone herbicides and triazolopyrimidine herbicides. In sulfonylurea herbicides the sulfonamide moiety is a component in a sulfonylurea bridge ($—S(O)_2NHC(O)NH(R)—$). In sulfonylurea herbicides the sulfonyl end of the sulfonylurea bridge is connected either directly or by way of an oxygen atom or an optionally substituted amino or methylene group to a typically substituted cyclic or acyclic group. At the opposite end of the sulfonylurea bridge, the amino group, which may have a substituent such as methyl (R being $CH_3$) instead of hydrogen, is connected to a heterocyclic group, typically a symmetric pyrimidine or triazine ring, having one or two substituents such as methyl, ethyl, trifluoromethyl, methoxy, ethoxy, methylamino, dimethylamino, ethylamino and the halogens. In sulfonylaminocarbonyltriazolinone herbicides, the sulfonamide moiety is a component of a sulfonylaminocarbonyl bridge ($—S(O)_2NHC(O)—$). In sulfonylaminocarbonyltriazolinone herbicides the sulfonyl end of the sulfonylaminocarbonyl bridge is typically connected to substituted phenyl ring. At the opposite end of the sulfonylaminocarbonyl bridge, the carbonyl is connected to the 1-position of a triazolinone ring, which is typically substituted with groups such as alkyl and alkoxy. In triazolopyrimidine herbicides the sulfonyl end of the sulfonamide moiety is connected to the 2-position of a substituted [1,2,4]triazolopyrimidine ring system and the amino end of the sulfonamide moiety is connected to a substituted aryl, typically phenyl, group or alternatively the amino end of the sulfonamide moiety is connected to the 2-position of a substituted [1,2,4]triazolopyrimidine ring system and the sulfonyl end of the sulfonamide moiety is connected to a substituted aryl, typically pyridinyl, group.

The methods further comprise applying to the crop and the weeds in a field a sufficient amount of at least one herbicide to which the crop seeds or plants are tolerant, such as, for example, glyphosate, a hydroxyphenylpyruvatedioxygenase inhibitor (e.g., mesotrione or sulcotrione), a phytoene desaturase inhibitor (e.g., diflufenican), a pigment synthesis inhibitor, sulfonamide, imidazolinone, bialaphos, phosphinothricin, azafenidin, butafenacil, sulfosate, glufosinate, triazolopyrimidine, pyrimidinyloxy(thio)benzoate or sulonylaminocarbonyltriazolinone, an acetyl Co-A carboxylase inhibitor such as quizalofop-P-ethyl, a synthetic auxin such as quinclorac, KIH-485 or a protox inhibitor to control the weeds without significantly damaging the crop plants.

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a *Brassica* plant. Thus, in some embodiments, a weed is a non-crop plant or a non-crop species, while in some embodiments, a weed is a crop species which is sought to be eliminated from a particular area, such as, for example, an inferior and/or non-transgenic *Brassica* plant in a field planted with *Brassica* event DP-073496-4 or a non-*Brassica* crop plant in a field planted with DP-073496-4. Weeds can be classified into two major groups: monocots and dicots.

Many plant species can be controlled (i.e., killed or damaged) by the herbicides described herein. Accordingly, the methods of the invention are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp *sesbania* (*Sesbania exaltata*), sicklepod (*Senna obtusifolia*), Texas blueweed (*Helianthus ciliaris*) and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass and a non-selective herbicide resistant ryegrass. In some embodiments, the undesired plants are proximate the crop plants.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95% or more of the weeds are significantly damaged or killed, while if crop plants are also present in the field, less than 45%, 40%, 35%, 30%, 25%, 20%, 15%, 10%, 5% or 1% of the crop plants are significantly damaged or killed.

In some embodiments, a *Brassica* DP-073496-4 plant of the invention is not significantly damaged by treatment with a particular herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000 or more grams or ounces (1 ounce=29.57 ml) of active ingredient or commercial product or herbicide formulation per acre or per hectare, whereas an appropriate control plant is significantly damaged by the same treatment.

In specific embodiments, an effective amount of an ALS inhibitor herbicide comprises at least about 0.1, 1, 5, 10, 25, 50, 75, 100, 150, 200, 250, 300, 350, 400, 450, 500, 600, 700, 750, 800, 850, 900, 950, 1000, 2000, 3000, 4000, 5000 or more grams or ounces (1 ounce=29.57 ml) of active ingredient per hectare. In other embodiments, an effective amount of an ALS inhibitor comprises at least about 0.1-50, about 25-75, about 50-100, about 100-110, about 110-120, about 120-130, about 130-140, about 140-150, about 150-200, about 200-500, about 500-600, about 600-800, about 800-1000 or greater grams or ounces (1 ounce=29.57 ml) of active ingredient per hectare. Any ALS inhibitor, for example, those listed in Table 1 can be applied at these levels.

In other embodiments, an effective amount of a sulfonylurea comprises at least 0.1, 1, 5, 10, 25, 50, 75, 100, 150, 200, 250, 300, 350, 400, 450, 500, 600, 700, 800, 900, 1000, 5000 or more grams or ounces (1 ounce=29.57 ml) of active ingredient per hectare. In other embodiments, an effective amount of a sulfonylurea comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000 or more grams or ounces (1 ounce=29.57 ml) of active ingredient per hectare. Representative sulfonylureas that can be applied at this level are set forth in Table 1.

In other embodiments, an effective amount of a sulfonylaminocarbonyltriazolinones, triazolopyrimidines, pyrimidinyloxy(thio)benzoates, and imidazolinones can comprise at least about 0.1, 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1550, 1600, 1650, 1700, 1800, 1850, 1900, 1950, 2000, 2500, 3500, 4000, 4500, 5000 or greater grams or ounces (1 ounce=29.57 ml) active ingredient per hectare. In other embodiments, an effective amount of a sulfonylaminocarbonyltriazolines, triazolopyrimidines, pyrimidinyloxy(thio)benzoates or imidazolinones comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000 or more grams or ounces (1 ounce=29.57 ml) active ingredient per hectare.

Additional ranges of the effective amounts of herbicides can be found, for example, in various publications from University Extension services. See, for example, Bernards, et al., (2006) *Guide for Weed Management in Nebraska* (www.ianrpubs.url.edu/sendlt/ec130); Regher, et al., (2005) *Chemical Weed Control for Fields Crops, Pastures, Rangeland, and Noncropland*, Kansas State University Agricultural Extension Station and Corporate Extension Service; Zollinger, et al., (2006) *North Dakota Weed Control Guide*, North Dakota Extension Service and the Iowa State University Extension at www.weeds.iastate.edu, each of which is herein incorporated by reference.

In some embodiments of the invention, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28 and 30 ounces of acid equivalent per acre at the lower end of the range of application and between 12, 14, 16, 18, 20, 22, 24, 26, 28, 30 and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). In some embodiments of the invention, a sulfonylurea herbicide is applied to a field and/or to at least one plant in a field at rates between 0.04 and 1.0 ounces of active ingredient per acre, or at rates between 0.1, 0.2, 0.4, 0.6 and 0.8 ounces of active ingredient per acre at the lower end of the range of application and between 0.2, 0.4, 0.6, 0.8 and 1.0 ounces of active ingredient per acre at the higher end of the range of application. (1 ounce=29.57 ml).

As is known in the art, glyphosate herbicides as a class contain the same active ingredient, but the active ingredient is present as one of a number of different salts and/or formulations. However, herbicides known to inhibit ALS vary in their active ingredient as well as their chemical formulations. One of skill in the art is familiar with the determination of the amount of active ingredient and/or acid equivalent present in a particular volume and/or weight of herbicide preparation.

In some embodiments, an ALS inhibitor herbicide is employed. Rates at which the ALS inhibitor herbicide is applied to the crop, crop part, seed or area of cultivation can be any of the rates disclosed herein. In specific embodiments, the rate for the ALS inhibitor herbicide is about 0.1 to about 5000 g ai/hectare, about 0.5 to about 300 g ai/hectare or about 1 to about 150 g ai/hectare.

Generally, a particular herbicide is applied to a particular field (and any plants growing in it) no more than 1, 2, 3, 4, 5, 6, 7 or 8 times a year, or no more than 1, 2, 3, 4 or 5 times per growing season.

By "treated with a combination of" or "applying a combination of" herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. In some embodiments, weeds which are susceptible to each of the herbicides exhibit damage from treatment with each of the herbicides which is additive or synergistic. The application of each herbicide and/or chemical may be simultaneous or the applications may be at different times, so long as the desired effect is achieved. Furthermore, the application can occur prior to the planting of the crop.

The proportions of herbicides used in the methods of the invention with other herbicidal active ingredients in herbicidal compositions are generally in the ratio of 5000:1 to 1:5000, 1000:1 to 1:1000, 100:1 to 1:100, 10:1 to 1:10 or 5:1 to 1:5 by weight. The optimum ratios can be easily determined by those skilled in the art based on the weed control spectrum desired. Moreover, any combinations of ranges of the various herbicides disclosed in Table 1 can also be applied in the methods of the invention.

Thus, in some embodiments, the invention provides improved methods for selectively controlling weeds in a field wherein the total herbicide application may be less than 90%, 85%, 80%, 75%, 70%, 65%, 60%, 55%, 50%, 45%, 40%, 35%, 30%, 25%, 20%, 15%, 10%, 5% or 1% of that used in other methods. Similarly, in some embodiments, the amount of a particular herbicide used for selectively controlling weeds in a field may be less than 90%, 85%, 80%, 75%, 70%, 65%, 60%, 55%, 50%, 45%, 40%, 35%, 30%, 25%, 20%, 15%, 10%, 5% or 1% of the amount of that particular herbicide that would be used in other methods, i.e., methods not utilizing a plant of the invention.

In some embodiments, a DP-073496-4 *Brassica* plant of the invention benefits from a synergistic effect, wherein the herbicide tolerance conferred by the GLYAT polypeptide and that conferred by a polypeptide providing tolerance to another herbicide is greater than expected from simply combining the herbicide tolerance conferred by each gene separately. See, e.g., McCutchen, et al., (1997) *J. Econ. Entomol.* 90:1170-1180; Priesler, et al., (1999) *J. Econ. Entomol.* 92:598-603. As used herein, the terms "synergy," "synergistic," "synergistically" and derivations thereof, such as in a "synergistic effect" or a "synergistic herbicide combination" or a "synergistic herbicide composition" refer to circumstances under which the biological activity of a combination of herbicides, such as at least a first herbicide and a second herbicide, is greater than the sum of the biological activities of the individual herbicides. Synergy, expressed in terms of a "Synergy Index (SI)," generally can be determined by the method described by Kull, et al., (1961) *Applied Microbiology* 9:538. See also, Colby, (1967) *Weeds* 15:20-22.

In other instances, the herbicide tolerance conferred on a DP-073496-4 plant of the invention is additive; that is, the herbicide tolerance profile conferred by the herbicide tolerance genes is what would be expected from simply combining the herbicide tolerance conferred by each gene separately to a transgenic plant containing them individually. Additive and/or synergistic activity for two or more herbicides against key weed species will increase the overall effectiveness and/or reduce the actual amount of active ingredient(s) needed to control said weeds. Where such synergy is observed, the plant of the invention may display tolerance to a higher dose or rate of herbicide and/or the plant may display tolerance to additional herbicides or other chemicals beyond those to which it would be expected to display tolerance. For example, a DP-073496-4 *Brassica* plant may show tolerance to organophosphate compounds such as insecticides and/or inhibitors of 4-hydroxyphenylpyruvate dioxygenase.

Thus, for example, the DP-073496-4 *Brassica* plants of the invention, when further comprising genes conferring tolerance to other herbicides, can exhibit greater than expected tolerance to various herbicides, including but not limited to glyphosate, ALS inhibitor chemistries and sulfonylurea herbicides. The DP-073496-4 *Brassica* plant plants of the invention may show tolerance to a particular herbicide or herbicide combination that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400% or 500% or more higher than the tolerance of an appropriate control plant that contains only a single herbicide tolerance gene which confers tolerance to the same herbicide or herbicide combination. Thus, DP-073496-4 *Brassica* plants may show decreased damage from the same dose of herbicide in comparison to an appropriate control plant, or they may show the same degree of damage in response to a much higher dose of herbicide than the control plant. Accordingly, in specific embodiments, a particular herbicide used for selectively containing weeds in a field is more than 1%, 5%, 10%, 15%, 20%, 25%, 30%, 35%, 40%, 45%, 50%, 60%, 70%, 80%, 90%, 100% or greater than the amount of that particular herbicide that would be used in other methods, i.e., methods not utilizing a plant of the invention.

In the same manner, in some embodiments, a DP-073496-4 *Brassica* plant of the invention shows improved tolerance to a particular formulation of a herbicide active ingredient in comparison to an appropriate control plant. Herbicides are sold commercially as formulations which typically include other ingredients in addition to the herbicide active ingredient; these ingredients are often intended to enhance the efficacy of the active ingredient. Such other ingredients can include, for example, safeners and adjuvants (see, e.g., Green and Foy, (2003) "Adjuvants: Tools for Enhancing Herbicide Performance," in *Weed Biology and Management*, ed. Inderjit (Kluwer Academic Publishers, The Netherlands)). Thus, a DP-073496-4 *Brassica* plant of the invention can show tolerance to a particular formulation of a herbicide (e.g., a particular commercially available herbicide product) that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, 500%, 600%, 700%, 800%, 900%, 1000%, 1100%, 1200%, 1300%, 1400%, 1500%, 1600%, 1700%, 1800%, 1900% or 2000% or more higher than the tolerance of an appropriate control plant that contains only a single herbicide tolerance gene which confers tolerance to the same herbicide formulation.

In some embodiments, a DP-073496-4 *Brassica* plant of the invention shows improved tolerance to a herbicide or herbicide class to which at least one other herbicide tolerance gene confers tolerance as well as improved tolerance to at least one other herbicide or chemical which has a different mechanism or basis of action than either glyphosate or the herbicide corresponding to said at least one other herbicide tolerance gene. This surprising benefit of the invention finds use in methods of growing crops that comprise treatment with various combinations of chemicals, including, for example, other chemicals used for growing crops. Thus, for example, a DP-073496-4 *Brassica* plant may also show improved tolerance to chlorpyrifos, a systemic organophosphate insecticide. Thus, the invention also provides a DP-073496-4 *Brassica* plant that confers tolerance to glyphosate (i.e., a GLYAT gene) which shows improved tolerance to chemicals which affect the cytochrome P450 gene, and methods of use thereof. In some embodiments, the DP-073496-4 *Brassica* plants also show improved tolerance to dicamba. In these embodiments, the improved tolerance to dicamba may be evident in the presence of glyphosate and a sulfonylurea herbicide.

In other methods, a herbicide combination is applied over a DP-073496-4 *Brassica* plant, where the herbicide combination produces either an additive or a synergistic effect for controlling weeds. Such combinations of herbicides can allow the application rate to be reduced, a broader spectrum of undesired vegetation to be controlled, improved control of the undesired vegetation with fewer applications, more rapid onset of the herbicidal activity or more prolonged herbicidal activity.

An "additive herbicidal composition" has a herbicidal activity that is about equal to the observed activities of the individual components. A "synergistic herbicidal combination" has a herbicidal activity higher than what can be expected based on the observed activities of the individual components when used alone. Accordingly, the presently disclosed subject matter provides a synergistic herbicide combination, wherein the degree of weed control of the mixture exceeds the sum of control of the individual herbicides. In some embodiments, the degree of weed control of the mixture exceeds the sum of control of the individual herbicides by any statistically significant amount including, for example, about 1% to 5%, about 5% to about 10%, about 10% to about 20%, about 20% to about 30%, about 30% to 40%, about 40% to about 50%, about 50% to about 60%, about 60% to about 70%, about 70% to about 80%, about 80% to about 90%, about 90% to about 100%, about 100% to 120% or greater. Further, a "synergistically effective amount" of a herbicide refers to the amount of one herbicide necessary to elicit a synergistic effect in another herbicide present in the herbicide composition. Thus, the term "synergist," and derivations thereof, refer to a substance that enhances the activity of an active ingredient (ai), i.e., a substance in a formulation from which a biological effect is obtained, for example, a herbicide.

Accordingly, in some embodiments, the presently disclosed subject matter provides a method for controlling weeds in an area of cultivation. In some embodiments, the method comprises: (a) planting the area with a DP-073496-4 crop seeds or crop plants which also comprise polynucleotides conferring ALS-inhibitor tolerance; and (b) applying to the weed, the crop plants, a crop part, the area of cultivation or a combination thereof, an effective amount of a herbicide composition comprising at least one of a synergistically effective amount of glyphosate and a synergistically effective amount of an ALS inhibitor (for example, but not limited to, a sulfonylurea herbicide) or agriculturally suitable salts thereof, wherein at least one of: (i) the synergistically effective amount of the glyphosate is lower than an amount of glyphosate required to control the weeds in the absence of the sulfonylurea herbicide; (ii) the synergistically effective amount of the ALS inhibitor herbicide is lower than an amount of the ALS inhibitor required to control the weeds in the absence of glyphosate and (iii) combinations thereof and wherein the effective amount of the herbicide composition is tolerated by the crop seeds or crop plants and controls the weeds in the area of cultivation.

In some embodiments, the herbicide composition used in the presently disclosed method for controlling weeds comprises a synergistically effective amount of glyphosate and a sulfonylurea herbicide. In further embodiments, the presently disclosed synergistic herbicide composition comprises glyphosate and a sulfonylurea herbicide selected from the group consisting of metsulfuron-methyl, chlorsulfuron and triasulfuron.

In particular embodiments, the synergistic herbicide combination further comprises an adjuvant such as, for example, an ammonium sulfate-based adjuvant, e.g., ADD-UP® (Wenkem., Halfway House, Midrand, South Africa). In additional embodiments, the presently disclosed synergistic herbicide compositions comprise an additional herbicide, for example, an effective amount of a pyrimidinyloxy(thio) benzoate herbicide. In some embodiments, the pyrimidinyloxy(thio)benzoate herbicide comprises bispyribac, e.g., (VELOCITY®, Valent U.S.A. Corp., Walnut Creek, Calif., United States of America) or an agriculturally suitable salt thereof.

In some embodiments of the presently disclosed method for controlling undesired plants, the glyphosate is applied pre-emergence, post-emergence or pre- and post-emergence to the undesired plants or plant crops and/or the ALS inhibitor herbicide (i.e., the sulfonylurea herbicide) is applied pre-emergence, post-emergence or pre- and post-emergence to the undesired plants or plant crops. In other embodiments, the glyphosate and/or the ALS inhibitor herbicide (i.e., the sulfonylurea herbicide) are applied together or are applied separately. In yet other embodiments, the synergistic herbicide composition is applied, e.g., step (b) above, at least once prior to planting the crop(s) of interest, e.g., step (a) above.

Weeds that can be difficult to control with glyphosate alone in fields where a crop is grown (such as, for example, a brassica crop) include but are not limited to the following: horseweed (e.g., Conyza *canadensis*); rigid ryegrass (e.g., *Lolium rigidum*); goosegrass (e.g., *Eleusine indica*); Italian ryegrass (e.g., *Lolium multiflorum*); hairy fleabane (e.g., Conyza *bonariensis*); buckhorn plantain (e.g., *Plantago lanceolata*); common ragweed (e.g., *Ambrosia artemisifolia*); morning glory (e.g., *Ipomoea* spp.); waterhemp (e.g., *Amaranthus* spp.); field bindweed (e.g., *Convolvulus arvensis*); yellow nutsedge (e.g., *Cyperus esculentus*); common lambsquarters (e.g., *Chenopodium album*); wild buckwheat (e.g., *Polygonium convolvulus*); velvetleaf (e.g., *Abutilon theophrasti*); *kochia* (e.g., *Kochia scoparia*) and Asiatic dayflower (e.g., *Commelina* spp.). In areas where such weeds are found, *Brassica* plants comprising the DP-073496-4 event and tolerance to another herbicide are particularly useful in allowing the treatment of a field (and therefore any crop growing in the field) with combinations of herbicides that would cause unacceptable damage to crop plants that did not contain both of these polynucleotides. Plants of the invention that are tolerant to glyphosate and other herbicides such as, for example, sulfonylurea, imidazolinone, triazolopyrimidine, pyrimidinyl(thio)benzoate and/or sulfonylaminocarbonyltriazolinone herbicides in addition to being tolerant to at least one other herbicide with a different mode of action or site of action are particularly useful in situations where weeds are tolerant to at least two of the same herbicides to which the plants are tolerant. In this manner, plants of the invention make possible improved control of weeds that are tolerant to more than one herbicide.

For example, some commonly used treatments for weed control in fields where current commercial crops (including, for example, *Brassicas*) are grown include glyphosate and, optionally, 2,4-D; this combination, however, has some disadvantages. Particularly, there are weed species that it does not control well and it also does not work well for weed control in cold weather. Another commonly used treatment for weed control in brassica fields is the sulfonylurea herbicide chlorimuron-ethyl, which has significant residual activity in the soil and thus maintains selective pressure on all later-emerging weed species, creating a favorable environment for the growth and spread of sulfonylurea-resistant weeds. Fields may be treated with sulfonylurea, imidazolinone, triazolopyrimidines, pyrimidiny(thio)benzoates and/or sulfonylaminocarbonyltriazonlinone such as the sulfonylurea chlorimuron-ethyl, either alone or in combination with other herbicides, such as a combination of glyphosate and tribenuron-methyl (available commercially as Express®). This combination has several advantages for weed control under some circumstances, including the use of herbicides with different modes of action and the use of herbicides having a relatively short period of residual activity in the soil. A herbicide having a relatively short period of residual activity is desirable, for example, in situations where it is important to reduce selective pressure that would favor the growth of herbicide-tolerant weeds. Of course, in any particular situation where weed control is required, other considerations may be more important, such as, for example, the need to prevent the development of and/or appearance of weeds in a field prior to planting a crop by using a herbicide with a relatively long period of residual activity. Treatments that include both tribenuron-methyl and thifensulfuron-methyl may be particularly useful.

Other commonly used treatments for weed control in fields where current commercial varieties of crops (including, for example, *Brassicas*) are grown include the sulfonylurea herbicide thifensulfuron-methyl (available commercially as Harmony GT®). However, one disadvantage of thifensulfuron-methyl is that the higher application rates required for consistent weed control often cause injury to a crop growing in the same field. DP-073496-4 *Brassica* plants comprising additional tolerance can be treated with a combination of glyphosate and thifensulfuron-methyl, which has the advantage of using herbicides with different modes of action. Thus, weeds that are resistant to either herbicide alone are controlled by the combination of the two herbicides, and the improved DP-073496-4 *Brassica* plants would not be significantly damaged by the treatment.

Other herbicides which are used for weed control in fields where current commercial varieties of crops (including, for example, *Brassicas*) are grown are the triazolopyrimidine herbicide cloransulam-methyl (available commercially as FirstRate®) and the imidazolinone herbicide imazaquin (available commercially as Sceptor®). When these herbicides are used individually they may provide only marginal control of weeds. However, may be treated, for example, with a combination of glyphosate (e.g., Roundup® (glyphosate isopropylamine salt)), imazapyr (currently available commercially as Arsenal®), chlorimuron-ethyl (currently available commercially as Classic®), quizalofop-P-ethyl (currently available commercially as Assure II®) and fomesafen (currently available commercially as Flexstar®). This combination has the advantage of using herbicides with different modes of action. Thus, weeds that are tolerant to just one or several of these herbicides are controlled by the combination of the five herbicides. This combination provides an extremely broad spectrum of protection against the type of herbicide-tolerant weeds that might be expected to arise and spread under current weed control practices.

Fields containing the DP-073496-4 *Brassica* plants with additional herbicide tolerance may also be treated, for example, with a combination of herbicides including glyphosate, rimsulfuron, and dicamba or mesotrione. This combination may be particularly useful in controlling weeds which have developed some tolerance to herbicides which inhibit ALS. Another combination of herbicides which may be particularly useful for weed control includes glyphosate and at least one of the following: metsulfuron-methyl (commercially available as Ally®), imazapyr (commercially available as Arsenal®), imazethapyr, imazaquin and sulfentrazone. It is understood that any of the combinations discussed above or elsewhere herein may also be used to treat areas in combination with any other herbicide or agricultural chemical.

Some commonly-used treatments for weed control in fields where current commercial crops (including, for example, *Brassica*) are grown include glyphosate (currently available commercially as Roundup®), rimsulfuron (currently available commercially as Resolve® or Matrix®), dicamba (commercially available as Clarity®), atrazine and mesotrione (commercially available as Callisto®). These herbicides are sometimes used individually due to poor crop tolerance to multiple herbicides. Unfortunately, when used individually, each of these herbicides has significant disadvantages. Particularly, the incidence of weeds that are tolerant to individual herbicides continues to increase, rendering glyphosate less effective than desired in some situations. Rimsulfuron provides better weed control at high doses which can cause injury to a crop, and alternatives such as dicamba are often more expensive than other commonly-used herbicides Some commonly-used treatments for weed control in fields where current commercial crops are grown include glyphosate (currently available commercially as Roundup®), chlorimuron-ethyl, tribenuron-methyl, rimsulfuron (currently available commercially as Resolve® or Matrix®), imazethapyr, imazapyr and imazaquin. Unfortunately, when used individually, each of these herbicides has significant disadvantages. Particularly, the incidence of weeds that are tolerant to individual herbicides continues to increase, rendering each individual herbicide less effective than desired in some situations. However, DP-073496-4 *Brassica* with an additional herbicide tolerance trait can be treated with a combination of herbicides that would cause unacceptable damage to standard plant varieties, including combinations of herbicides that include at least one of those mentioned above.

In the methods of the invention, a herbicide may be formulated and applied to an area of interest such as, for example, a field or area of cultivation, in any suitable manner. A herbicide may be applied to a field in any form, such as, for example, in a liquid spray or as solid powder or granules. In specific embodiments, the herbicide or combination of herbicides that are employed in the methods comprise a tankmix or a premix. A herbicide may also be formulated, for example, as a "homogenous granule blend" produced using blends technology (see, e.g., U.S. Pat. No. 6,022,552, entitled "Uniform Mixtures of Pesticide Granules"). The blends technology of U.S. Pat. No. 6,022,552 produces a nonsegregating blend (i.e., a "homogenous granule blend") of formulated crop protection chemicals in a dry granule form that enables delivery of customized mixtures designed to solve specific problems. A homogenous granule blend can be shipped, handled, subsampled and applied in the same manner as traditional premix products where multiple active ingredients are formulated into the same granule.

Briefly, a "homogenous granule blend" is prepared by mixing together at least two extruded formulated granule products. In some embodiments, each granule product comprises a registered formulation containing a single active ingredient which is, for example, a herbicide, a fungicide and/or an insecticide. The uniformity (homogeneity) of a "homogenous granule blend" can be optimized by controlling the relative sizes and size distributions of the granules used in the blend. The diameter of extruded granules is controlled by the size of the holes in the extruder die and a centrifugal sifting process may be used to obtain a population of extruded granules with a desired length distribution (see, e.g., U.S. Pat. No. 6,270,025).

A homogenous granule blend is considered to be "homogenous" when it can be subsampled into appropriately sized aliquots and the composition of each aliquot will meet the required assay specifications. To demonstrate homogeneity, a large sample of the homogenous granule blend is prepared and is then subsampled into aliquots of greater than the minimum statistical sample size. Blends also afford the ability to add other agrochemicals at normal, labeled use rates such as additional herbicides (a $3^{rd}/4^{th}$ mechanism of action), fungicides, insecticides, plant growth regulators and the like thereby saving costs associated with additional applications.

Any herbicide formulation applied over the DP-073496-4 *Brassica* plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. For additional guidance regarding the art of formulation, see, Woods, "The Formulator's Toolbox—Product Forms for Modern Agriculture" *Pesticide Chemistry and Bioscience, The Food-Environment Challenge*, Brooks and Roberts, Eds., Proceedings of the 9th International Congress on Pesticide Chemistry, The Royal Society of Chemistry, Cambridge, 1999, pp. 120-133. See also, U.S. Pat. No. 3,235,361, Column 6, line 16 through Column 7, line 19 and Examples 10-41; U.S. Pat. No. 3,309,192, Column 5, line 43 through Column 7, line 62 and Examples 8, 12, 15, 39, 41, 52, 53, 58, 132, 138-140, 162-164, 166, 167 and 169-182; U.S. Pat. No. 2,891,855, Column 3, line 66 through Column 5, line 17 and Examples 1-4; Klingman, *Weed Control as a Science*, John Wiley and Sons, Inc., New York, 1961, pp 81-96 and Hance, et al., *Weed Control Handbook,* 8th Ed., Blackwell Scientific Publications, Oxford, 1989, each of which is incorporated herein by reference in their entirety.

The methods of the invention further allow for the development of herbicide combinations to be used with the DP-073496-4 *Brassica* plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment and tillage practices. Upon the evaluation of the environmental conditions, an effective amount of a combination of herbicides can be applied to the crop, crop part, seed of the crop or area of cultivation.

In some embodiments, the herbicide applied to the DP-073496-4 *Brassica* plants of the invention serves to prevent the initiation of growth of susceptible weeds and/or serve to cause damage to weeds that are growing in the area of interest. In some embodiments, the herbicide or herbicide mixture exert these effects on weeds affecting crops that are subsequently planted in the area of interest (i.e., field or area of cultivation). In the methods of the invention, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention. Thus, methods of the invention encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein).

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

Thus, the invention provides improved methods of growing a crop and/or controlling weeds such as, for example, "pre-planting burn down," wherein an area is treated with herbicides prior to planting the crop of interest in order to better control weeds. The invention also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The methods of the invention encompass the use of simultaneous and/or sequential applications of multiple classes of herbicides. In some embodiments, the methods of the invention involve treating a plant of the invention and/or an area of interest (e.g., a field or area of cultivation) and/or weed with just one herbicide or other chemical such as, for example, a sulfonylurea herbicide.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area. The stages of growth and/or development of plants are known in the art. Thus, for example, the time at which a herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

In some embodiments, the DP-073496-4 *Brassica* plants of the invention show improved tolerance to postemergence herbicide treatments. For example, plants of the invention may be tolerant to higher doses of herbicide, tolerant to a broader range of herbicides, and/or may be tolerant to doses of herbicide applied at earlier or later times of development in comparison to an appropriate control plant. For example, in some embodiments, the DP-073496-4 *Brassica* plants of the invention show an increased resistance to morphological defects that are known to result from treatment at particular stages of development. Thus, the glyphosate-tolerant plants of the invention find use in methods involving herbicide treatments at later stages of development than were previously feasible. Thus, plants of the invention may be treated with a particular herbicide that causes morphological defects in a control plant treated at the same stage of development, but the glyphosate-tolerant plants of the invention will not be significantly damaged by the same treatment.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of a herbicide; for example, generally, glyphosate has very little or no soil residual activity, while herbicides that act to inhibit ALS vary in their residual activity levels. Residual activities for various herbicides are known in the art, and are also known to vary with various environmental factors such as, for example, soil moisture levels, temperature, pH and soil composition (texture and organic matter).

Moreover, the transgenic plants of the invention provide improved tolerance to treatment with additional chemicals commonly used on crops in conjunction with herbicide treatments, such as safeners, adjuvants such as ammonium sulfonate and crop oil concentrate, and the like. The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and US Patent Application Publication Numbers 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the invention can involve the use of herbicides in combination with herbicide safeners such as benoxacor, BCS (1-bromo-4-[(chloromethyl) sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this invention, or applied as seed treatments. Therefore an aspect of the present invention relates to the use of a mixture comprising glyphosate, at least one other herbicide and an antidotally effective amount of a herbicide safener.

Seed treatment is particularly useful for selective weed control, because it physically restricts antidoting to the crop plants. Therefore a particularly useful embodiment of the present invention is a method for selectively controlling the growth of weeds in a field comprising treating the seed from which the crop is grown with an antidotally effective amount of safener and treating the field with an effective amount of herbicide to control weeds. Antidotally effective amounts of safeners can be easily determined by one skilled in the art through simple experimentation. An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

In specific embodiments, the herbicide or herbicide combination applied to the plant of the invention acts as a safener. In this embodiment, a first herbicide or a herbicide mixture is applied at an antidotally effect amount to the plant. Accordingly, a method for controlling weeds in an area of cultivation is provided. The method comprises planting the area with crop seeds or plants which comprise a first polynucleotide encoding a polypeptide that can confer tolerance to glyphosate operably linked to a promoter active in a plant; and, a second polynucleotide encoding an ALS inhibitor-tolerant polypeptide operably linked to a promoter active in a plant. A combination of herbicides comprising at least an effective amount of a first and a second herbicide is applied to the crop, crop part, weed or area of cultivation thereof. The effective amount of the herbicide combination controls weeds; and, the effective amount of the first herbicide is not tolerated by the crop when applied alone when compared to a control crop that has not been exposed to the first herbicide; and, the effective amount of the second herbicide is sufficient to produce a safening effect, wherein the safening effect provides an increase in crop tolerance upon the application of the first and the second herbicide when compared to the crop tolerance when the first herbicide is applied alone.

In specific embodiments, the combination of safening herbicides comprises a first ALS inhibitor and a second ALS inhibitor. In other embodiments, the safening effect is achieved by applying an effective amount of a combination of glyphosate and at least one ALS inhibitor chemistry. Such mixtures provides increased crop tolerance (i.e., a decrease in herbicidal injury). This method allows for increased application rates of the chemistries post or pre-treatment. Such methods find use for increased control of unwanted or undesired vegetation. In still other embodiments, a safening affect is achieved when the DP-073496-4 brassica crops, crop part, crop seed, weed or area of cultivation is treated with at least one herbicide from the sulfonylurea family of chemistry in combination with at least one herbicide from the imidazolinone family. This method provides increased crop tolerance (i.e., a decrease in herbicidal injury). In specific embodiments, the sulfonylurea comprises rimsulfuron and the imidazolinone comprises imazethapyr. In other embodiments, glyphosate is also applied to the crop, crop part or area of cultivation.

As used herein, an "adjuvant" is any material added to a spray solution or formulation to modify the action of an agricultural chemical or the physical properties of the spray solution. See, for example, Green and Foy, (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners and wetting agents.

In addition, methods of the invention can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus or fungi to form a multi-component mixture giving an even broader spectrum of agricultural protection. Examples of such agricultural protectants which can be used in methods of the invention include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. The weight ratios of these various mixing partners to other compositions (e.g., herbicides) used in the methods of the invention typically are between 100:1 and 1:100, or between 30:1 and 1:30, between 10:1 and 1:10, or between 4:1 and 1:4.

The present invention also pertains to a composition comprising a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC375839), myclobutanil, neo-asozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV and granulosis virus (GV) such as CpGV. Methods of the invention may also comprise the use of plants genetically transformed to express proteins toxic to invertebrate pests (such as *Bacillus thuringiensis* delta-endotoxins). In such embodiments, the effect of exogenously applied invertebrate pest control compounds may be synergistic with the expressed toxin proteins.

General references for these agricultural protectants include *The Pesticide Manual, 13th Edition*, Tomlin, Ed., British Crop Protection Council, Farnham, Surrey, U.K., 2003 and *The BioPesticide Manual, 2nd Edition*, Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this invention can also provide a broader spectrum of plant protection and be advantageous for resistance management.

Thus, methods of the invention employ a herbicide or herbicide combination and may further comprise the use of insecticides and/or fungicides, and/or other agricultural chemicals such as fertilizers. The use of such combined treatments of the invention can broaden the spectrum of activity against additional weed species and suppress the proliferation of any resistant biotypes.

Methods of the invention can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl and plant growth modifying organisms such as *Bacillus cereus* strain BP01.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXPERIMENTAL

The following abbreviations are used in describing the present invention.

| | |
|---|---|
| ALS | acetolactate synthase protein |
| bp | base pair |
| glyat4621 | glyphosate acetyltransferase gene |
| GLYAT4621 | glyphosate acetyltransferase protein |
| zm-als | wild type acetolactate synthase gene from *brassica* |
| zm-hra | modified version of acetolactate synthase gene from *brassica* |
| kb | kilobase |
| PCR | polymerase chain reaction |
| UTR | untranslated region |

Example 1. Insert and Flanking Border Sequence Characterization of *Brassica* Event DP0-73496-4

*Brassica* (*Brassica napus* L.) has been modified by the insertion of the glyphosate acetyltransferase gene (glyat4621) derived from *Bacillus licheniformis* and optimized by gene shuffling. Plasmid PHP28181 contains an expression cassette as further described hereafter.

DNA construct PHP28181 was made by cloning the GAT4621:PINII TERM fragment excised from DNA construct pZSL149 with BamHI and MfeI double digestion downstream to the AT-UBQ10 promoter of DNA construct QC272 in the same BamHI and MfeI sites using T4 DNA ligase (New England Lab). The resulting PHP28181 DNA contains the expression cassette: AT-UBQ10 (DUPONT) PRO:GAT4621:PINII TERM. See, FIG. 1 and FIG. 2.

The 2112 bp PHP28181A DNA fragment was prepared from plasmid PHP28181 with HindIII and NotI restriction enzyme double digestion. The digested plasmid DNA was resolved in a 1% agarose gel by electrophoresis. The DNA band of the correct size was excised and DNA fragment was extracted using a Qiagen DNA fragment extraction kit (Qiagen). DNA fragment purity was checked by PCR with a series of dilutions of amp+ positive control DNA since the PHP28181 plasmid contains an amp+ gene in its backbone. DNA fragment concentration was measured spectrophotometrically and confirmed by comparing to DNA low mass markers (InVitrogen) in an agarose gel.

Transformation was accomplished essentially as described in Chen and Tulsieram, US Patent Application Publication Number 2007/0107077. Buds were collected from donor line NS1822BC and sterilized. Buds were then homogenized, filtered, and washed to collect the microspores. The resultant microspore suspension was adjusted to a specified density and cultured for 2 days. Embryogenic microspores were then isolated via gradient centrifugation and cultured.

Gold particles coated with the PHP28181A DNA fragment were used for transformation. Biolistic transformation was carried out using the PDS-1000/He Particle Delivery System (Bio-Rad, Hercules, Calif.) as described by Klein, et al., (1987) *Nature* 327:70-73. Transformed embryogenic microspores were cultured in fresh medium in dark conditions for 10-12 days, then under dim light for 1-3 weeks. Green embryos were transferred to fresh medium and cultured for two weeks to select for glyphosate tolerance. Germinated shoots and/or plants were transferred to growth medium supplemented with glyphosate.

The glyat4621 gene was derived from the soil bacterium *Bacillus licheniformis* and was synthesized by a gene shuffling process to optimize the acetyltransferase activity of the GLYAT4621 enzyme (Castle, et al., (2004) *Science* 304: 1151-1154).

The inserted fragment (FIG. 3) from this plasmid contains the glyat4621 gene cassette. The expression of the glyat4621 gene is controlled by the UBQ10 regulatory region from *Arabidopsis* and the pinII terminator (see, Table 4). A summary of the transformation fragment of plasmid PHP28181 is shown in Table 4. The genetic elements of plasmid PHP28181 used in the creation of DP-073496-4 are shown in Table 3.

TABLE 3

Description of Genetic Elements in Plasmid PHP28181

| Region | Location on plasmid (base pair position) | Known Genetic Element | Size (base pairs) | Description |
|---|---|---|---|---|
| Transformation Fragment PHP28181A | 1 to 2112 | | 2112 | See Table 4 for information on the elements in this region |
| Plasmid Construct | 2113 to 4770 | includes elements below | 2658 | DNA from various sources for plasmid construction and plasmid replication |
| | 2736 to 3596 | bla ($Ap^R$) | 861 | β-lactamase gene coding for ampicillin resistance from *E. coli* (Sutcliiffe, 1978) (Yanisch-Perron, et al., 1984) |
| | 4170 to 4539 | colE1 ori | 370 | Hae II fragment containing bacterial origin of replication region (colE1 derived) (Tomizawa et al., 1977) |

TABLE 4

Description of Genetic Elements in the Transformation Fragment PHP28181A

| Location on Fragment (base pair position) | Genetic Element | Size (base pairs) | Description |
|---|---|---|---|
| 1 to 7 | Polylinker Region | 7 | Region required for cloning genetic elements |
| 8 to 1312 | UBQ10 Promoter | 1305 | Version of the promoter region from *Arabidopsis thaliana* UBQ10 polyubiquitin gene (Norris et al., 1993) developed by the E. I. duPont de Nemours and Company |
| 1313 to 1335 | Polylinker Region | 23 | Region required for cloning genetic elements |
| 1336 to 1779 | gat4621 Gene | 444 | Synthetic glyphosate N-acetyltransferase gene (Castle et al., 2004; Siehl et al., 2007) |
| 1780 to 1796 | Polylinker Region | 17 | Region required for cloning genetic elements |
| 1797 to 2106 | pinII Terminator | 310 | Terminator region from *Solanum tuberosum* proteinase inhibitor II gene (Keil et al., 1986; An et al., 1989) |
| 2107 to 2112 | Polylinker Region | 6 | Region required for cloning genetic elements |

The nucleotide sequence of the inserted DNA in the DP-073496-4 event has been determined. PCR amplification of the unique junctions spanning the introduced genetic elements can distinguish DP-073496-4 plants from their non-genetically-modified counterparts and can be used to screen for the presence of the inserted DNA, even at very low concentrations. Described below is a construct-specific polymerase chain reaction (PCR) assay on genomic DNA from DP-073496-4 *Brassica.*

Specifically, genomic DNA from the test substance (plant material of event DP-073496-4) and the control substance (plant material of a non-genetically modified *Brassica* with a genetic background representative of the event background) is isolated and subjected to qualitative PCR amplification using a construct-specific primer pair. The PCR products are separated on 1.5% or 2% agarose gels to confirm the presence of the inserted construct in the genomic DNA generated from the test substance, and absence in the genomic DNA generated from the control substance. A reference standard (100 base pair DNA Ladder; Invitrogen Corporation Catalog #10380-012) is used to determine the PCR product size.

Test and control samples are harvested from plants. Genomic DNA extraction from the test and control tissues is performed using a standard urea extraction protocol, if leaf tissue. Genomic DNA from the test and control samples is isolated using Wizard® Magnetic 96 DNA Plant System (Promega Corporation Catalog # FF3760), if seed tissue. Genomic DNA is quantified on a spectrofluorometer using PicoGreen® reagent (Molecular Probes, Inc., Eugene, Oreg.) and/or visualized on an agarose gel to confirm quantitation values and to determine the DNA quality.

Genomic DNA isolated from plant material of event DP-073496-4 and control samples is subjected to PCR amplification (PCR Master Mix Catalog #7505 from Promega Corporation) utilizing a construct-specific primer pair which spans at least a portion of the glyat4621 coding region, and allows for the unique identification of maize event DP-073496-4. A second primer set is used to amplify an endogenous gene as a positive control for PCR amplification. The PCR target site and size of the expected PCR product for each primer set are compared to the observed results.

Example 2. Characterization of Event DP-073496-4 by Southern Blot

Southern blot analyses (Southern, 1975) are performed to investigate the number of sites of insertion of the transforming DNA, the copy number and functional integrity of the genetic elements and the absence of plasmid backbone sequences.

The method used is described generally as follows. Genomic DNA is extracted from lyophilized tissue sampled from DP-073496-4 *Brassica* and non-genetically-modified control plants. Genomic DNA is digested with restriction endonuclease enzymes and size-separated on an agarose gel. A molecular weight marker is run alongside samples for size estimation purposes. DNA fragments separated on agarose gel are depurinated, denatured and neutralized in situ and transferred to a nylon membrane. Following transfer to the membrane, the DNA is bound to the membrane by UV crosslinking. Fragments homologous to the glyat4621 gene are generated by PCR from plasmid PHP28181, separated on an agarose gel by size, excised and purified using a gel extraction kit. Labeled probe is hybridized to the target DNA on the nylon membranes for detection of the specific fragments. Washes after hybridization are carried out at high stringency. Blots are exposed to X-ray film for one or more time points to detect hybridizing fragments and visualize molecular weight markers.

Example 3. Expression of the Insert

Expression of the GLYAT4621 protein is evaluated using leaf tissue collected from transgenic plants. For example, four fresh leaf punches may be collected and ground in sample extraction buffer using a GenoGrinder (Spex Certiprep). Total Extractable Protein (TEP) can be determined using the Bio-Rad Protein assay, which is based on the Bradford dye-binding procedure. Sample extracts may be diluted in sample extraction buffer for ELISA analysis.

The levels of expression of the GAT4621 protein in DP-073496-4 *Brassica* can be determined by quantitative enzyme linked immunosorbent assay (ELISA) of samples obtained from multiple field trial locations. Replicate seed samples (three replicates) may be obtained from DP-073496-4 plants treated with the maximum recommended label rate of Touchdown® Total glyphosate herbicide (500 g/l glyphosate as potassium salt; 0.60-1.35 l/ha), applied at the cotyledon to 6-leaf stage, as this represents a likely commercial cultivation scenario.

Another way to verify the expression of the insert in DP-073496-4 *Brassica* plants is to evaluate the transformed plants' tolerance to glyphosate. Multigenerational stability and within-generation segregation of the herbicide tolerant trait conferred by expression of the GAT4621 enzyme will be confirmed using a functional assay for herbicide tolerance. Tests are conducted on at least three generations of plant material. Herbicide injury may be scored as described in Table 5.

TABLE 5

The 0 to 100 crop response rating system for herbicide injury

| Rating | Main categories | Detailed description |
|---|---|---|
| 0 | No Effect | No crop reduction or injury |
| 10 | Slight Effect | Slight crop discoloration or stunting |
| 20 | | Some crop discoloration, stunting, or stunt loss |
| 30 | | Crop injury more pronounced, but not lasting |
| 40 | Moderate Effect | Moderate injury, crop usually recovers |
| 50 | | Crop injury more lasting, recovery doubtful |
| 60 | | Lasting crop injury, no recovery |
| 70 | Severe Effect | Heavy crop injury and stand loss |
| 80 | | Crop nearly destroyed - A few surviving plants |
| 90 | | Only occasional live crop plants left |
| 100 | Complete Effect | Complete crop destruction |

Example 4. Construct Specific PCR Analysis of *Brassica* Event DP-073496-4

Genomic DNA isolated from leaf of DP-073496-4 canola (T2F2 generation) and control canola (non-genetically modified) was subjected to PCR amplification (Roche High Fidelity PCR Master Kit, Roche Catalog #12140314001) utilizing the construct-specific primer pair (09-0-3290/09-0-3288) which spans the ubiquitin promoter and the gat4621 gene cassette (FIG. 4). A second primer set (09-0-2812/09-0-2813) was used to amplify the endogenous canola FatA gene as a positive control for PCR amplification. The PCR target site and size of the expected PCR product for each primer sets are shown in Table 8. PCR reagents and reaction conditions are shown in Table 9. The primer sequences used in this study are listed in Table 10. In this study, 100 ng of leaf genomic DNA was used in all PCR reactions.

A PCR product of approximately 600 bp in size amplified by the construct-specific primer set 09-0-3290/09-0-3288 was observed in PCR reactions using plasmid PHP28181 (10 ng) as a template and three DP-073496-4 canola plants, but absent in three control canola plants and the no-template control (FIG. 5). Samples were loaded as shown in Table 6.

TABLE 6

| Lane | Sample |
|---|---|
| 1 | Low Mass Molecular Weight Marker |
| 2 | Blank |
| 3 | Non-Genetically Modified canola C1 |
| 4 | Non-Genetically Modified canola C2 |
| 5 | Non-Genetically Modified canola C3 |
| 6 | DP-073496-4 canola T1 |
| 7 | DP-073496-4 canola T2 |
| 8 | DP-073496-4 canola T3 |
| 9 | NT Control |
| 10 | Plasmid PHP28181 |
| 11 | Blank |
| 12 | Low Mass Molecular Weight Marker |

These results correspond with the expected PCR product size (675 bp) for samples containing DP-073496-4 canola genomic DNA. A PCR product approximately 450 bp in size was observed for both DP-073496-4 canola and control canola plants following PCR reaction with the primer set 09-0-2812/09-0-2813 for detection of the endogenous FatA gene (FIG. 6). Samples were loaded as shown in Table 7.

TABLE 7

| Lane | Sample |
|---|---|
| 1 | Low Mass Molecular Weight Marker |
| 2 | Blank |
| 3 | Non-Genetically Modified canola C1 |
| 4 | Non-Genetically Modified canola C2 |
| 5 | Non-Genetically Modified canola C3 |
| 6 | DP-073496-4 canola T1 |
| 7 | DP-073496-4 canola T2 |
| 8 | DP-073496-4 canola T3 |
| 9 | NT Control |
| 10 | Plasmid PHP28181 |
| 11 | Blank |
| 12 | Low Mass Molecular Weight Marker |

These results correspond with the expected PCR product size (506 bp) for genomic DNA samples containing the canola endogenous FatA gene. The endogenous target band was not observed in the no-template control.

TABLE 8

PCR Genomic DNA Target Site and Expected Size of PCR Products

| Primer Set | Target Site | Expected Size of PCR Product (bp) |
|---|---|---|
| 09-0-3290/09-0-3288 | Construct-Specific ubiquitin promoter and gat4621 | 675 |
| 09-0-2812/09-0-2813 | Endogenous canola FatA gene[1] | 506 |

PCR: POLYMERASE CHAIN REACTION
BP: BASE PAIRS
[1]Genbank accession number for FatA gene is X87842.1. This sequence was used to design PCR primers.

TABLE 9

PCR Reagents and Reaction Conditions

| PCR Reagents | | PCR Reaction Conditions | | | |
|---|---|---|---|---|---|
| Reagent | Volume (μL) | Cycle Element | Temp (° C.) | Time (sec) | # Cycles |
| Template DNA (100 ng/μl) | 1 | Initial Denaturation | 94 | 120 | 1 |
| Primer 1 (10 μM) | 0.75 | Denaturation | 94 | 10 | |
| Primer 2 (10 μM) | 0.75 | Annealing | 65 | 20 | 35 |
| PCR Master Mix* | 12.5 | Elongation | 72 | 45 | |
| $ddH_2O$ | 10 | Final Elongation | 72 | 180 | 1 |
| | | Hold Cycle | 4 | Until analysis | |

PCR: POLYMERASE CHAIN REACTION
$DDH_2O$: DOUBLE-DISTILLED WATER
*Roche High Fidelity Master Mix

TABLE 10

List of Primer Sequences Used in PCR Reactions

| Primer Name | Sequence 5' - 3' | Target Sequence |
|---|---|---|
| 09-0-3290 | SEQ ID NO 4: AGCTATTGCTTCACCGCCTTAGC | Ubiquitin Promoter |

TABLE 10-continued

List of Primer Sequences Used in PCR Reactions

| Primer Name | Sequence 5' - 3' | Target Sequence |
|---|---|---|
| 09-0-3288 | SEQ ID NO: 5<br>GCTCAGCTTGGTGGAATGAAGCCAC | gat4621 |
| 09-0-2812 | SEQ ID NO: 6<br>GACACAAGGCGGCTTCAAAGAGTTACAGATG | Canola Endogenous FatA |
| 09-0-2813 | SEQ IC NO 7:<br>ACAATGTCATCTTGCTGGCATTCTCTTCTG | Canola Endogenous FatA |

Example 5. Further Insert and Flanking Border Sequence Characterization of *Brassica* Event DP-073496-4

To characterize the integrity of the inserted DNA and the genomic insertion site, the flanking genomic DNA border regions of the DP-073496-4 event were determined. Flanking genomic sequence of DP-073496-4 is included within SEQ ID NO: 2. PCR amplification from the insert and border sequences confirms that the border regions are of *Brassica* origin and that the junction regions can be used for identification of DP-073496-4 *Brassica*. Overall, characterization of the insert and genomic border sequences, along with Southern blot data, indicate a single insertion of the DNA fragment present in the *Brassica* genome. Various molecular techniques are then used to specifically characterize the integration site.

In the initial characterization, the flanking genomic border regions are cloned and sequenced using the GenomeWalker and inverse PCR methods. Using information from the flanking border sequence, PCR is performed on DP-073496-4 genomic DNA and unmodified control genomic DNA. Those skilled in the art will also include a control PCR using an endogenous gene to verify that the isolated genomic DNA is suitable for PCR amplification.

TABLE 12

Summary Table of SEQ ID NOS

| SEQ ID NO | Description |
|---|---|
| 1 | GAT4621 protein |
| 2 | DP-073496-4 insert and flanking sequence |
| 3 | PHP28181A |
| 4 | Primer 09-0-3290 (SEQ ID NO: 4 AGCTATTGCTTCACCGCCTTAGC) Target - Ubiquitin Promoter |
| 5 | Primer 09-0-3288 (SEQ ID NO: 5 GCTCAGCTTGGTGGAATGAAGCCAC) Target gat4621 |
| 6 | Primer 09-0-2812 (SEQ ID NO: 6 GACACAAGGCGGCTTCAAAGAGTTACAGATG) Target Canola Endogenous FatA |
| 7 | Primer 09-0-2813 (SEQ ID NO: ACAATGTCATCTTGCTGGCATTCTCTTCTG ) Canola Endogenous FatA |
| 8 | Right border genomic sequence |
| 9 | Left border genomic sequence |
| 10 | Complete internal transgene |
| 11 | Complete flanking and internal transgene |
| 12 | Right flanking genomic/right border transgene (10 nt/10 nt) |
| 13 | Left flanking genomic/left border transgene (10 nt/10 nt) |
| 14 | Right flanking genomic/right border transgene (20 nt/20 nt) |
| 15 | Left flanking genomic/left border transgene (20 nt/20 nt) |

TABLE 11

| PCR-based event-specific detection methods | PCR Assay | Primer 1 | | Primer 2 | | Probe | | | |
|---|---|---|---|---|---|---|---|---|---|
| event | type | Name | Sequence | Name | Sequence | Name | Sequence | 5' label | Quencher |
| DP-073496-4 | Gel base | 10-0-3514 SEQ ID NO: 20 | GGTCCGTGGGCCTTCCTAAACGTGCCG | 10-0-3515 SEQ ID NO: 23 | TTATCCGGTCCTAGATCATCAGTTCATACAAACCTCC | — | — | — | — |
| DP-073496-4 | Real time | 09-0-2824 SEQ ID NO: 21 | GTTCTTCTCTTCATAGCTCATTACAGTTTT | 09-0 2825 SEQ ID NO: 24 | CAAACCTCCATAGAGTTCAACATCTTAA | 09-QP83 SEQ ID NO: 26 | TTAGTTAGATCAGGATATTCTTG | FAM | MGB |
| FatA A-specific | Real-time | 09-0-3249 SEQ ID NO: 22 | ACAGATGAAGTTCGGGACGAGGTAC | 09-0-3251 SEQ ID NO: 25 | CAGGTTGAGATCCACATGCTTAAATAT | 09-QP87 SEQ ID NO: 27 | AAGAAGAATCATCATGCTTC | FAM | MGB |

TABLE 12-continued

| Summary Table of SEQ ID NOS | |
|---|---|
| SEQ ID NO | Description |
| 16 | Right flanking genomic/right border transgene (30 nt/30 nt) |
| 17 | Left flanking genomic/left border transgene (30 nt/30 nt) |
| 18 | Right flanking genomic/complete transgene |
| 19 | Left flanking genomic/complete transgene |
| 20 | Primer 10-O-3514 |
| 21 | Primer 09-O-2824 |
| 22 | Primer 09-O-3249 |
| 23 | Primer 10-O-3515 |
| 24 | Primer 09-O-2825 |
| 25 | Primer 09-O-3251 |
| 26 | Primer 09-QP83 |
| 27 | Primer 09-QP87 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide comprising SEQ ID NO: 12 and 13.

2. The isolated polynucleotide of claim 1, wherein said polynucleotide comprises a nucleotide sequence set forth in SEQ ID NO:2, 11, 14, 15, 16 17, 18 or 19.

3. A DNA detection kit comprising at least one polynucleotide that can specifically detect a DP-073496-4 specific region, wherein the DP-073496-4 specific region comprises a polynucleotide having SEQ ID NO: 12 or 13.

* * * * *